United States Patent [19]

Pfister et al.

[11] Patent Number: 5,003,081
[45] Date of Patent: Mar. 26, 1991

[54] PYRROLE DERIVATIVES USEFUL AS DIAZO AND COUPLING COMPONENTS

[75] Inventors: Juergen Pfister, Speyer; Matthias Wiesenfeldt, Mutterstadt; Karl-Heinz Etzbach, Frankenthal, all of Fed. Rep. of Germany

[73] Assignee: BASF Aktiengesellschaft, Ludwigshafen, Fed. Rep. of Germany

[21] Appl. No.: 461,688

[22] Filed: Jan. 8, 1990

[30] Foreign Application Priority Data

Jan. 26, 1989 [DE] Fed. Rep. of Germany ....... 3902216

[51] Int. Cl.$^5$ .................. C07D 207/44; C07D 401/04; C07D 401/06; C07D 403/02
[52] U.S. Cl. ..................................... 548/524; 548/518; 548/523; 548/527; 548/539; 548/540; 548/541; 548/558; 548/559; 540/602; 546/208; 546/281; 544/58.6; 544/60; 544/141; 544/272
[58] Field of Search ............... 548/524, 527, 541, 558, 548/559, 523, 518, 539, 540

[56] References Cited
U.S. PATENT DOCUMENTS 4,737,513 4/1988 Tessier et al. ...................... 548/558

FOREIGN PATENT DOCUMENTS 126389 7/1977 Fed. Rep. of Germany ...... 548/524

*Primary Examiner*—Mary C. Lee
*Assistant Examiner*—J. Richter
*Attorney, Agent, or Firm*—Oblon, Spivak, McClelland, Maier & Neustadt

[57] ABSTRACT

Pyrrole derivatives of the formula

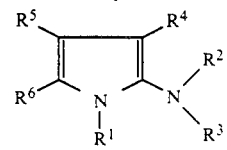

or the tautomers thereof, where
$R^1$ is hydrogen, alkyl, alkenyl, alkynyl, cycloalkyl, phenyl, hetaryl or amino, it being possible for these radicals to be substituted,
$R^2$ is hydrogen, alkyl, benzyl, alkenyl, cycloalkyl or phenyl
$R^3$ is hydrogen, alkyl, benzyl or alkenyl, or $R^2$ and $R^3$ together are

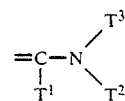

where $T^1$, $T^2$ and $T^3$ have the meanings mentioned in the description, or $R^2$ and $R^3$ together with the nitrogen connecting them are a heterocyclic radical,
$R^4$ is cyano, or carbamoyl or thiocarbamoyl, each of which can be substituted, or $-C(NH_2)=N-OH$.
$R^5$ is halogen, hydroxyl, alkanoyloxy or benzoyloxy and
$R^6$ is hydrogen, alkyl, phenyl, cyano, halogen, nitro, hydroxysulfonyl, alkanoyl, benzoyl or

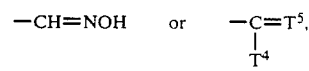

where $T^4$ is alkyl or phenyl and $T^5$ is the radical of an active methylene compound, hydroxyimino or the radical of a primary amine,
with the proviso that $R^1$, $R^2$ and $R^3$ are not all hydrogen, a process for the preparation of pyrrole derivatives (with $R^5$=hydroxyl) and the use of the novel products as diazo or coupling components are described.

4 Claims, No Drawings

PYRROLE DERIVATIVES USEFUL AS DIAZO AND COUPLING COMPONENTS

The present invention relates to compounds of the general formula I

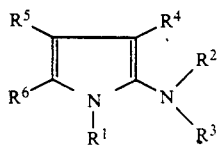

or the tautomers thereof, where $R^1$ is hydrogen, $C_1$-$C_{20}$-alkyl which can be substituted and/or interrupted by one or more oxygens, $C_3$-$C_6$-alkenyl which can be substituted, $C_3$-$C_6$-alkynyl which can be substituted, $C_3$-$C_{10}$-cycloalkyl which can be substituted, phenyl which can be substituted, pyridyl, thienyl, amino, $C_1$-$C_4$-alkanoylamino, benzoylamino, $C_1$-$C_4$-dialkylamino or

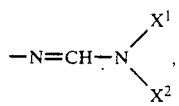

where $X^1$ is $C_1$-$C_4$-alkyl or phenyl, and $X^2$ is $C_1$-$C_4$-alkyl, alkyl, $R^2$ is hydrogen, $C_1$-$C_4$-alkyl, benzyl, $C_3$14 $C_6$-alkenyl, $C_5$-$C_7$-cycloalkyl, or phenyl which can be substituted, $R^3$ is hydrogen, $C_1$-$C_4$-alkyl, benzyl or $C_3$-$C_6$-alkenyl, or $R^2$ and $R^3$ together are

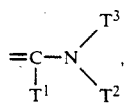

where $T^1$ is hydrogen, $C_1$-$C_4$-alkyl or phenyl, $T^2$ is $C^1$-$C_4$-alkyl, or phenyl which can be substituted, and $T^3$ is $C_1$-$C_4$-alkyl, or $R^2$ and $R^3$ together with the nitrogen connecting them are a 5- to 7-membered saturated heterocyclic radical which can contain other hetero atoms.

$R^4$ is cyano, carbamoyl, $C_1$-$C_4$-mono- or dialkylcarbamoyl, thiocarbamoyl, $C_1$-$C_4$-mono- or dialkylthiocarbamoyl or

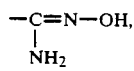

$R^5$ is halogen, hydroxyl, $C_1$-$C_{20}$-alkanoyloxy, or benzoyloxy which can be substituted, and $R^6$ is hydrogen, $C_1$-$C_4$-alkyl, phenyl which can be substituted, cyano, halogen, nitro, hydroxysulfonyl, $C_1$-$C_{10}$-alkanoyl, benzoyl which can be substituted, or

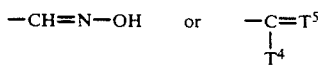

where $T^4$ is $C_1$-$C_4$-alkyl, or phenyl which can be substituted, and $T^5$ is the radical of an active methylene compound, hydroxyimino or $N$—$X^3$ where $X^3$ is $C_1$-$C_{20}$-alkyl which can be substituted and/or interrupted by one or more oxygens, $C_3$-$C_6$-alkenyl which can be substituted, $C_3$-$C_6$-alkynyl which can be substituted, $C_3$-$C_{10}$-cycloalkyl which can be substituted, phenyl which can be substituted, pyridyl, $C_1$-$C_4$-alkoxycarbonylmethyl, amino, $C_1$-$C_4$-dialkylamino or phenylamino, with the proviso that $R^1$, $R^2$ and $R^3$ are not all hydrogen.

DD-A-126,389 discloses 5-methyl- and 5-ethyl-2-amino-3-cyanopyrrolin-4-one. However, these compounds are not particularly suitable as diazo components for the preparation of azo dyes.

The object of the present invention was to prepare novel pyrrole derivatives which are suitable, depending on the constitution, both as diazo components and as coupling components.

In accordance with this, we have found the pyrrole derivatives of the formula I which are identified in the introduction.

All the alkyls and alkenyls occurring in the above-mentioned formula I can be both straight-chain and branched.

When alkyls which are interrupted by one or more oxygens occur in the formula I, the preferred alkyls are interrupted by one to three, in particular one or two, oxygens.

When substituted phenyls occur in the formula I, examples of suitable substituents are $C_1$-$C_4$-alkyl, $C_1$-$C_4$-alkoxy, halogen, especially chlorine or bromine, nitro, hydroxyl or amino.

When substituted alkyls occur in the formula I, examples of suitable substituents are $C_1$-$C_5$-alkylthio, phenoxy which can be substituted, halogen, especially chlorine or bromine, hydroxyl, amino, $C_1$-$C_4$-mono- or dialkylamino, pyrrolidino, piperidino, morpholino, thiomorpholino, piperazino, $N$-($C_1$-$C_4$-alkyl)piperazino, hexamethyleneimino, $C_1$-$C_5$-alkoxycarbonyl, or phenyl which can be substituted.

When substituted alkenyls, alkynyls or cycloalkyls occur in the formula I, examples of suitable substituents are fluorine, chlorine or bromine.

When $R^2$ and $R^3$ together with the nitrogen connecting them are a 5- to 7-membered saturated heterocyclic radical which can contain further hetero atoms, suitable examples are pyrrolidino, piperidino, morpholino, thiomorpholino, thiomorpholino S,S-dioxide, piperazino, $N$-($C_1$-$C_4$-alkyl)piperazino or hexamethyleneimino.

Examples of $R^1$ are hydrogen, methyl, ethyl, propyl, isopropyl, butyl, isobutyl, sec-butyl, pentyl, isopentyl, neopentyl, tert-pentyl, hexyl, heptyl, octyl, isooctyl, 2-ethylhexyl, nonyl, isononyl, decyl, isodecyl, undecyl, dodecyl, tridecyl, isotridecyl, tetradecyl, pentadecyl, hexadecyl, heptadecyl, octadecyl, nonadecyl, eicosyl, allyl, propinyl, methallyl, cyclopropyl, cyclobutyl, cyclopentyl, cyclohexyl, cycloheptyl, cyclooctyl, cyclononyl, cyclodecyl, 2-hydroxyethyl, 2-methoxyethyl, 2-ethoxyethyl, 2- or 3-hydroxypropyl, 2- or 3-methoxypropyl, 2- or 3-ethoxypropyl, 2- or 3-(2-phenoxyethoxy)propyl, 2- or 3-benzyloxypropyl, 2-methylthioethyl, 2-ethylthioethyl, 2- or 3-methylthiopropyl, 2- or 3-ethylthiopropyl, 2-aminoethyl, 2-(N,N-dimethylamino)ethyl, 2-(N,N-diethylamino)ethyl, 2- or 3-(N,N-dimethylamino)propyl, 2- or 3-(N,N-diethylamino)propyl, 2- or 3-aminopropyl, benzyl, 1-phenylethyl, 2-phenylethyl, phenyl, 2-hydroxyphenyl, 3-hydroxyphenyl, 4-hydroxyphenyl, 2-methoxyphenyl, 3-methoxyphenyl, 4-methoxyphenyl, 2-ethoxyphenyl, 3-ethoxyphenyl, 4-ethoxyphenyl, 2-chlorophenyl, 3-chlorophenyl, 4-chlorophenyl, 2-nitrophenyl, 3-nitrophenyl, 4-nitrophenyl, 2-aminophenyl, 3-aminophenyl, 4-aminophenyl, 2-methylphenyl, 3-methylphenyl, 4-methylphenyl 2-ethylphenyl, 3-ethylphenyl, 4-ethylphenyl, pyrid-2-yl, pyrid-3-yl, pyrid-4-yl, methoxycarbonylmethyl, ethoxycarbonylmethyl, propoxycarbonylmethyl, butoxycarbonylmethyl, 2-methoxycarbonylethyl, 2-ethoxycarbonylethyl, 2-propoxycarbonylethyl, 2-butoxycarbonylethyl, 2-(3,4-dichlorophenyl)ethyl, diphenylmethyl, 2-(3-chloro-2-methylphenyl)ethyl, 2-(3,4-dimethoxyphenyl)ethyl, 2-(2-chlorophenyl)ethyl, amino, dimethylamino, diethylamino, thien-2-yl, 2-morpholinoethyl, 2- or 3-morpholinopropyl or 2-piperazinoylethyl. (The terms isooctyl, isononyl, isodecyl and isotridecyl used above are trivial names and derive from the alcohols obtained in the oxo synthesis—cf. in this connection Ullmanns Enzyklopädie der technischen Chemie, 4th edition, volume 7, pages 215 to 217, and volume 11, pages 435 and 436.

Examples of $R^2$ and $R^3$ are methyl, ethyl, propyl, isopropyl, butyl, isobutyl, sec-butyl or allyl.

Examples of $R^5$ are chlorine, bromine, acetyloxy, propionyloxy, butyryloxy, isobutyryloxy, hexanoyloxy or benzoyloxy.

Examples of $R^6$ are methyl, ethyl, formyl, acetyl, propionyl, butyryl, isobutyryl, pentanoyl, hexanoyl, benzoyl, chlorine or bromine.

—$NX^3$ is derived from primary amines of the formula $H_2NX^3$. Examples of these which may be mentioned are methylamine, ethylamine, propylamine, isopropylamine, butylamine, isobutylamine, sec-butylamine, tert-butylamine, pentylamine, isopentylamine, neopentylamine, hexylamine, heptylamine, n-octylamine, isooctylamine, 2-ethylhexylamine, nonylamine, isononylamine, decylamine, isodecylamine, undecylamine, dodecylamine, tridecylamine, isotridecylamine, tetradecylamine, pentadecylamine, hexadecylamine, heptadecylamine, octadecylamine, nonadecylamine eicosylamine, allylamine, methallylamine, propargylamine, cyclopropylamine, cyclobutylamine, cyclopentylamine, cyclohexylamine, cycloheptylamine, cyclooctylamine, cyclononylamine, cyclodecylamine, 2-hydroxyethylamine, 2-methoxyethylamine, 2-ethoxyethylamine, 3-hydroxypropylamine, 3-methoxypropylamine, 3-ethoxypropylamine, 3-(2-phenoxyethoxy)propylamine, 3-benzyloxypropylamine, 2-(N,N-dimethylamino)ethylamine, 2-(N,N-diethylamino)ethylamine, 3-(N,N-dimethylamino)propylamine, 3-(N,N-diethylamino)propylamine, benzylamine, 2-phenylethylamine, 3-phenylpropylamine, aniline, 2-hydroxyaniline, 3-hydroxyaniline, 4-hydroxyaniline, o-anisidine, m-anisidine, p-anisidine, o-phenetidine, m-phenetidine, p-phenetidine, 2-chloroaniline, 3-chloroaniline, 3-nitroaniline, 4-nitroaniline, o-toluidine, m-toluidine, p-toluidine, 1,2-phenylenediamine, 1,3-phenylenediamine, 1,4-phenylenediamine, 2-ethylaniline, 3-ethylaniline, 4-ethylaniline, 2-aminopyridine, 3-aminopyridine, 4-aminopyridine, glycine methyl ester, glycine ethyl ester, glycine propyl ester, glycine butyl ester, hydrazine, N,N-dimethylhydrazine or phenylhydrazine.

$T^5$ is derived from active methylene compounds of the formula $H_2T^5$. Examples of such compounds are those of the formula

where $Z^3$ is hydrogen, cyano, nitro, $C_1$–$C_6$-alkanoyl, benzoyl, $C_1$–$C_4$-alkylsulfonyl, phenylsulfonyl, carboxyl, $C_1$–$C_4$-alkoxycarbonyl, carbamoyl or $C_1$–$C_4$-mono- or dialkylcarbamoyl, or of the formula

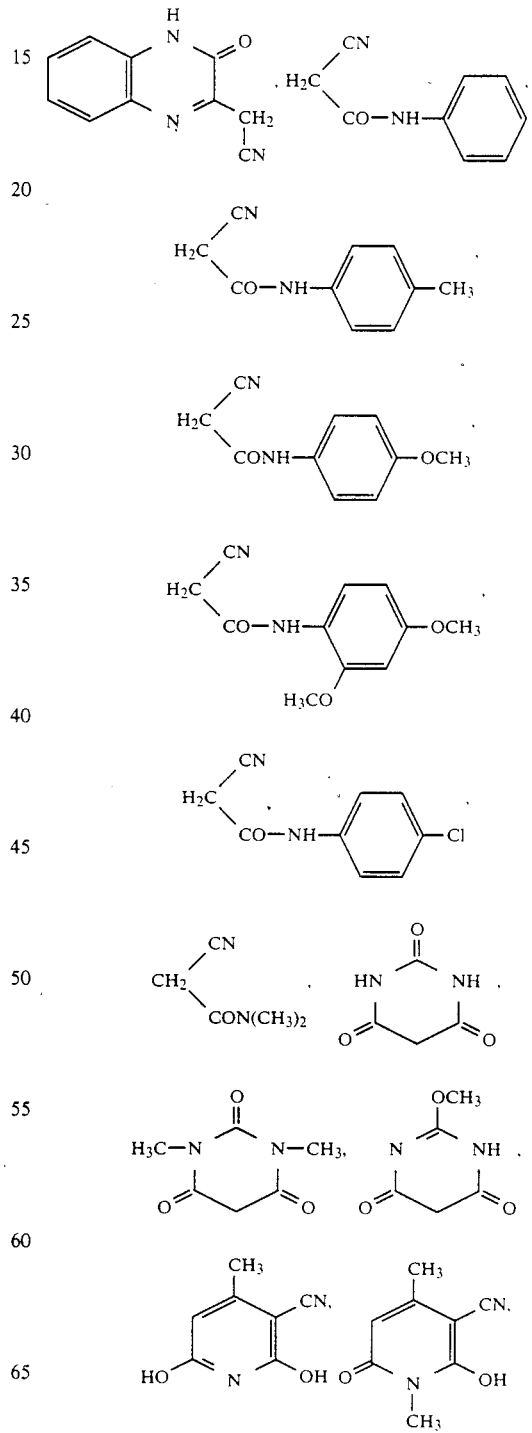

Some particularly important compounds are, e.g.:

Pyrrole derivatives of the formula Ia or Ib (Ia)

-continued

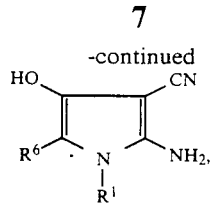
(Ib)

where $R^1$, $R^2$, $R^3$ and $R^6$ each have the abovementioned meanings, are advantageously prepared by reacting the compound of the formula II

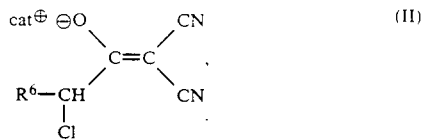
(II)

where $R^6$ has the abovementioned meaning, and cat⊕ is a cation (e.g. an alkali metal ion or, preferably, a trialkylammonium ion), with an amine of the formula IIIa or IIIb

(IIIa)

$R^1—NH_2$, (IIIb)

where $R^1$, $R^2$ and $R^3$ each have the abovementioned meanings.

The reaction is expediently carried out in an inert solvent (e.g. N,N-dimethylformamide, N,N-dimethylacetamide, N-methylpyrrolidinone, hexamethylphosphoric trisamide, 1,3-dimethylimidazolidin-2-one, 1,3-dimethylhexahydropyrimidin-2-one or 1,2-diethoxyethane) in the presence of a base (e.g. triethylamine, tripropylamine, tributylamine, N-methylpiperidine or N,N-dimethylaniline) at from 0° to 150° C. The molar ratio of compound III to amine is 1:1 to 1:5 as a rule.

The compound of the formula II can be prepared in a conventional manner from malononitrile and the carbonyl chloride of the formula IV

(IV)

where $R^6$ has the abovementioned meaning.

The pyrrole derivatives of the formula Ia and Ib can be reacted by conventional methods (e.g. by the Vilsmeier reaction) to give further compounds of the formula I.

Further details of the preparation can be taken from the Examples.

The novel pyrrole derivatives of the formula I are suitable, depending on the constitution, as diazo or coupling components for azo dyes.

Preferred pyrrole derivatives of the formula I are those where $R^1$ is hydrogen, $C_1$–$C_{15}$-alkyl, $C_5$–$C_7$-cycloalkyl, $C_3$–$C_5$-alkenyl, $C_2C_5$-hydroxyalkyl, $C_2$–$C_5$-halogenoalkyl, $C_1$–$C_5$-alkoxy-$C_2$–$C_5$-alkyl, phenoxy-$C_2$–$C_5$-alkoxy-$C_2$–$C_5$-alkyl, phenyl-$C_1$–$C_5$-alkoxy-$C_2$–$C_5$-alkoxy-$C_2$–$C_5$-alkyl, $C_1$–$C_5$-alkylthio-$C_2$–$C_5$-alkyl, $C_1$–$C_5$-dialkylamino-$C_2$–$C_2$-alkyl, phenyl-$C_1$–$C_5$-alkyl, $C_1$–$C_5$-alkoxycarbonyl-$C_1C_5$-alkyl, $—(CH_2)_n—Y$ where n is from 1 to 5 and Y is pyrrolidino, piperidino, morpholino, thiomorpholino, piperazino, N-($C_1$–$C_4$-alkyl)piperazino or hexamethyleneimino, or phenyl, pyridyl, amino or $C_1$–$C_5$-dialkylamino, $R^2$ is hydrogen, $C_1$–$C_4$-alkyl, allyl, benzyl or phenyl,
$R^3$ is hydrogen, $C_1$–$C_4$-alkyl, allyl or benzyl, or $R^2$ and $R^3$ together are

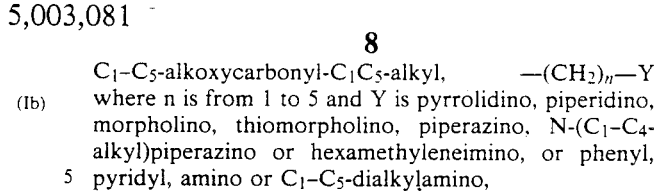

where $T^1$ is hydrogen or $C_1$–$C_4$-alkyl, $T^2$ is $C_1$–$C_4$-alkyl or phenyl, and $T^3$ is $C_1$–$C_4$-alkyl, or $R^2$ and $R^3$ together with the nitrogen connecting them are pyrrolidino, piperidino, morpholino, thiomorpholino, piperazino, N-($C_1$–$C_4$-alkyl)piperazino or hexamethyleneimino, $R^4$ is cyano, carbamoyl, thiocarbamoyl or

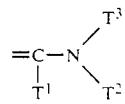

$R^5$ is fluorine, chlorine, bromine, hydroxyl, $C_1$–$C_6$-alkanoyloxy or benzoyloxy and $R^6$ is hydrogen, $C_1$–$C_4$-alkyl, phenyl, $C_1$–$C_6$-alkanoyl, benzoyl, cyano, chlorine, bromine, nitro, hydroxysulfonyl or

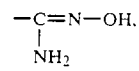

where $T^4$ and $T^5$ each have the abovementioned meanings.

Particularly preferred pyrrole derivatives of the formula I are those in which $R^1$ is hydrogen, $C_1$–$C_{10}$-alkyl, $C_3$–$C_4$-alkenyl, benzyl, phenyl or amino, $R^2$ is hydrogen, $C_1$–$C_4$-alkyl, allyl, benzyl or phenyl,
$R^3$ is hydrogen $C_1$–$C_4$-alkyl or allyl, or $R^2$ and $R^3$ together with the nitrogen connecting the nitrogen connecting them are pyrrolidino, piperidino, morpholino, thiomorpholino, N-methylpiperazino or hexamethyleneimino, $R^4$ is cyano, carbamoyl, thiocarbamoyl or

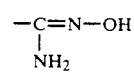

$R^5$ is chlorine, bromine, hydroxyl, $C_1$–$C_6$-alkanoyloxy or benzoyloxy and $R^6$ is hydrogen, $C_1$–$C_4$-alkyl, phenyl, $C_1$–$C_6$-alkanoyl, benzoyl, cyano or

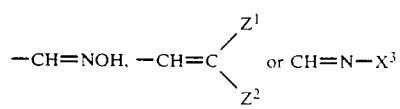

where $Z^1$ and $Z^2$ are identical or different and, independently of one another, are each cyano, $C_1$–$C_4$-alkoxycarbonyl or nitro, and $X^3$ has the abovementioned meaning.

Of special interest are pyrrole derivatives of the formula I where $R^1$ is $C_1$–$C_4$-alkyl, phenyl or amino and
$R^2$ and $R^3$ are each hydrogen or
$R^1$ is hydrogen,
$R^2$ is methyl, ethyl, allyl, benzyl or phenyl,
$R^3$ is methyl, ethyl or allyl or $R^2$ and $R^3$ together with the nitrogen connecting them are pyrrolidino, piperidino, morpholino, N-methylpiperazino or hexamethyleneimino,
$R^4$ is cyano or carbamoyl,
$R^5$ is chlorine, bromine or hydroxyl,
$R^6$ is hydrogen, formyl, cyano or

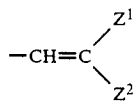

where $Z^1$ and $Z^2$ are identical or different and, independently of one another, are each cyano, $C_1$–$C_4$-alkyl, $C_1$–$C_4$-alkoxycarbonyl or nitro.

Particularly important pyrrole derivatives in this connection are those in which the radicals $Z^1$ and $Z^2$ are, independently of one another, cyano or $C_1$–$C_4$-alkoxycarbonyl or else one of the two radicals is hydrogen.

The Examples which follow are intended to illustrate the invention.

EXAMPLE 1

2-Amino-3-cyano-1-methyl-pyrrolin-4-one 99 g of malononitrile were dissolved in 150 ml of N,N-dimethylformamide (DMF) and cooled to 0° C. While cooling, 556 g of tributylamine and 169.5 g of chloroacetyl chloride were simultaneously added dropwise to this, and the mixture was then stirred at 10° C. for 10 minutes. The reaction mixture was subsequently added to a mixture of 1.5 kg of ice and 327 ml of 40% by weight aqueous methylamine solution and stirred at room temperature for 8 hours. The precipitate was filtered off with suction, washed and dried in an oven at 50° C. 124 g (60% of theory) of the compound of the formula

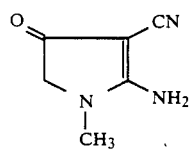 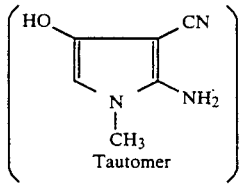

of melting point 300° C. were obtained. The IR, NMR, UV and mass spectra and the elemental analysis are consistent with the structural formula.

EXAMPLE 2

2-Amino-3-cyano-1-ethylpyrrolin-4-one 19.8 g of malononitrile were dissolved in 30 ml of DMF and cooled to 0° C. While cooling, 61 g of triethylamine and 32 g of chloroacetyl chloride were simultaneously added dropwise to this, and the mixture was then stirred at 10° C. for 10 minutes. Subsequently, while cooling, 49 g of 70% by weight aqueous ethylamine solution were added dropwise, and the mixture was stirred at room temperature for 8 hours. The precipitate was filtered off with suction, washed and dried at 50° C. 41.8 g (92%) of impure crude product were obtained and were recrystallized from 1:1 isopropanol/water with the addition of active carbon. This resulted in 10.9 g (24% of theory) of the compound of the formula

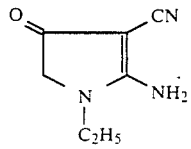

of melting point 278° to 280° C. The IR, NMR, UV and mass spectra and the elemental analysis are consistent with the structural formula.

EXAMPLE 3

2-Amino-3-cyano-1-isopropylpyrrolin-4-one 99 g of malononitrile were dissolved in 150 ml of DMF and cooled to 0° C. While cooling, 306 g of triethylamine and 159 g of chloroacetyl chloride were simultaneously added dropwise to this. The reaction mixture was stirred at 10° C. for 10 minutes and subsequently added to a mixture of 1.5 kg of ice and 158 g of isopropylamine. The mixture was stirred at room temperature for 8 hours. The volatiles were then removed by distillation under atmospheric pressure at 100° C., and the distillation residue was cooled to 5° C. The precipitate was filtered off with suction, washed and dried. 105.6 g (43% of theory) of the compound of the formula

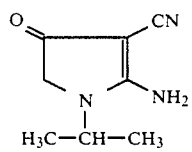

of melting point 285° to 290° C. were obtained. The IR, NMR, UV and mass spectra and the elemental analysis are consistent with the structural formula.

EXAMPLE 4

2-Amino-3-cyano-1-tridecylpyrrolin-4-one 19.8 g of malononitrile were dissolved in 30 ml of DMF and cooled to 0° C. While cooling, 61 g of triethylamine and 27 g of chloroacetyl chloride were simultaneously added dropwise to this, and the mixture was stirred at 10° C. for 10 minutes. 65.7 g of tridecylamine were then added dropwise, and the reaction mixture was stirred at room temperature for 48 hours. 300 ml of isopropylamine were then added to the mixture, which was refluxed for 2 hours, 10 g of active carbon were added, and the mixture was filtered hot. After cooling, the precipitate was filtered off with suction, washed and dried at 50° C. 40 g (44% of theory) of the compound of the formula

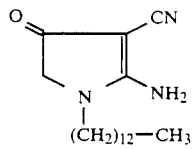

(CH₂)₁₂—CH₃ of melting point 214° to 215° C. were obtained. The IR, NMR, UV and mass spectra and the elemental analysis are consistent with the structural formula.

EXAMPLE 5

1-Allyl-2-amino-3-cyanopyrrolin-4-one 19.8 g of malononitrile were dissolved in 30 ml of DMF and cooled to 0° C. While cooling, 87 g of tributylamine and 27 g of chloroacetyl chloride were simultaneously added dropwise to this, and the mixture was stirred at 10° C. for 10 minutes. The mixture was then added to a mixture of 300 g of ice and 43 g of allylamine and stirred at room temperature for 8 hours. The precipitate was filtered off with suction, washed and dried. 38.1 g (78% of theory) of impure crude product were obtained and were boiled in 150 ml of isopropanol to purify. After cooling to 5° C., the precipitate was filtered off with suction, washed and dried. 31.2 g (64% of theory) of the compound of the formula

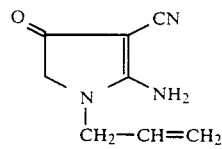

CH₂—CH=CH₂ of melting point 275° to 278° C. were obtained The IR, NMR, UV and mass spectra and the elemental analysis are consistent with the structural formula.

EXAMPLE 6

2-cyano-3-cyano-1-(2-methoxyethyl)pyrrolin-4-one 99 g of malononitrile were dissolved in 150 ml of DMF and cooled to 0° C. While cooling, 306 g of triethylamine and 159 g of chloroacetyl chloride were simultaneously added dropwise to this, and the mixture was stirred at 10° C. for 10 minutes. The mixture was then added to a mixture of 1.5 kg of ice and 291 g of 2-methoxyethylamine and stirred at room temperature for 8 hours. The volatiles were removed by distillation at 100° C. under atmospheric pressure, and the distillation residue was concentrated in a rotary evaporator at the water pump. The residue was recrystallized from 500 ml of isopropanol. The precipitate was filtered off with suction, washed and dried at 50° C. 205.5 g (76% of theory) of the compound of the formula

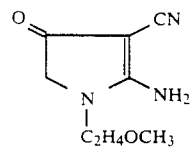

C₂H₄OCH₃ of melting point 108° to 110° C. were obtained. The IR, NMR, UV and mass spectra and the elemental analysis are consistent with the structural formula.

EXAMPLE 7

2-Amino-3-cyano-1-phenylpyrrolin-4-one Variant A 26.4 g of malononitrile were dissolved in 150 ml of DMF and cooled to 0° C. While cooling, 148 g of tributylamine and 45 g of chloracetyl chloride were simultaneously added dropwise to this, and the mixture was stirred at room temperature for 30 minutes. 42 g of aniline were then added to the mixture, which was stirred at 80° C. for 15 hours and then 200 g of water were added. After cooling to room temperature, the organic phase was separated off and digested with dichloromethane. The precipitate was filtered off with suction, washed and dried. 37.4 g (46% of theory) of the compound of the formula

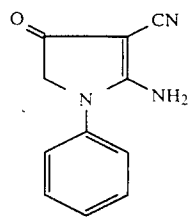

of melting point 285° to 290° C. were obtained. The IR, NMR, UV and mass spectra and the elemental analysis are consistent with the structural formula

Variant B 19.8 g of malononitrile were dissolved in 30 ml of DMF and cooled to 0° C. While cooling, 61 g of triethylamine and 27 g of chloracetyl chloride were simultaneously added dropwise to this, and the mixture was stirred at 10° C. for 10 minutes. 27.6 g of aniline were then added, and the reaction mixture was stirred at room temperature for 8 hours. 1 kg of water was added, and the mixture was then refluxed for 2 hours and cooled to 10° C., and the precipitate was filtered off with suction, washed and dried. 39.2 g (66% of theory) of the compound identical in all data to the product synthesized in Variant A) were obtained. The compounds listed in the following Table 1 are obtained in a similar manner.

TABLE 1

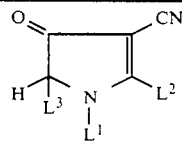

| Example No. | L¹ | L² | L³ | Melting point [°C.] |
|---|---|---|---|---|
| 8 | CH₂—CH(C₂H₅)—C₄H₉ | NH₂ | H | |
| 9 | n-C₃H₇ | NH₂ | H | 257-267 |
| 10 | n-C₄H₉ | NH₂ | H | 182-192 |

TABLE 1-continued $$\text{structure with } L^1, L^2, L^3, \text{CN, and O substituents on pyrrole ring}$$

| Example No. | $L^1$ | $L^2$ | $L^3$ | Melting point [°C.] |
|---|---|---|---|---|
| 11 | iso-C$_4$H$_9$ | NH$_2$ | H | |
| 12 | sec-C$_4$H$_9$ | NH$_2$ | H | |
| 13 | n-C$_5$H$_{11}$ | NH$_2$ | H | |
| 14 | Neo-C$_5$H$_{11}$ | NH$_2$ | H | |
| 15 | n-C$_6$H$_{13}$ | NH$_2$ | H | |
| 16 | n-C$_7$H$_{15}$ | NH$_2$ | H | |
| 17 | n-C$_8$H$_{17}$ | NH$_2$ | H | |
| 18 | n-C$_9$H$_{19}$ | NH$_2$ | H | |
| 19 | n-C$_{10}$H$_{21}$ | NH$_2$ | H | |
| 20 | n-C$_{11}$H$_{23}$ | NH$_2$ | H | |
| 21 | n-C$_{12}$H$_{25}$ | NH$_2$ | H | |
| 22 | n-C$_{14}$H$_{29}$ | NH$_2$ | H | |
| 23 | n-C$_{15}$H$_{31}$ | NH$_2$ | H | |
| 24 | n-C$_{16}$H$_{33}$ | NH$_2$ | H | |
| 25 | n-C$_{17}$H$_{35}$ | NH$_2$ | H | |
| 26 | n-C$_{18}$H$_{37}$ | NH$_2$ | H | |
| 27 | n-C$_{19}$H$_{39}$ | NH$_2$ | H | |
| 28 | n-C$_{20}$H$_{41}$ | NH$_2$ | H | |
| 29 | CH$_2$C≡CH | NH$_2$ | H | |
| 30 | Cyclo-C$_3$H$_5$ | NH$_2$ | H | |
| 31 | Cyclo-C$_4$H$_7$ | NH$_2$ | H | |
| 32 | Cyclo-C$_5$H$_9$ | NH$_2$ | H | |
| 33 | Cyclo-C$_6$H$_{11}$ | NH$_2$ | H | 300 |
| 34 | Cyclo-C$_7$H$_{13}$ | NH$_2$ | H | |
| 35 | Cyclo-C$_8$H$_{15}$ | NH$_2$ | H | |
| 36 | Cyclo-C$_9$H$_{17}$ | NH$_2$ | H | |
| 37 | Cyclo-C$_{10}$H$_{19}$ | NH$_2$ | H | |
| 38 | CH$_2$CH$_2$OH | NH$_2$ | H | 245–250 |
| 39 | CH$_2$CH$_2$OC$_2$H$_5$ | NH$_2$ | H | |
| 40 | CH$_2$CH$_2$NH$_2$ | NH$_2$ | H | |
| 41 | CH$_2$CH$_2$N(CH$_3$)$_2$ | NH$_2$ | H | |
| 42 | CH$_2$CH$_2$N(C$_2$H$_5$)$_2$ | NH$_2$ | H | |
| 43 | CH$_2$CH$_2$SCH$_3$ | NH$_2$ | H | |
| 44 | CH$_2$CH$_2$SC$_2$H$_5$ | NH$_2$ | H | |
| 45 | (CH$_2$)$_3$OH | NH$_2$ | H | |
| 46 | (CH$_2$)$_3$OCH$_3$ | NH$_2$ | H | |
| 47 | (CH$_2$)$_3$OC$_2$H$_5$ | NH$_2$ | H | |
| 48 | (CH$_2$)$_3$NH$_2$ | NH$_2$ | H | |
| 49 | (CH$_2$)$_3$N(CH$_3$)$_2$ | NH$_2$ | H | |
| 50 | (CH$_2$)$_3$N(C$_2$H$_5$)$_2$ | NH$_2$ | H | |
| 51 | (CH$_2$)$_3$SCH$_3$ | NH$_2$ | H | |
| 52 | (CH$_2$)$_3$SC$_2$H$_5$ | NH$_2$ | H | |
| 53 | CH$_2$C$_6$H$_5$ | NH$_2$ | H | 236–238 |
| 54 | CH$_2$CH$_2$C$_6$H$_5$ | NH$_2$ | H | 230–232 |
| 55 | CH(CH$_3$)C$_6$H$_5$ | NH$_2$ | H | |
| 56 | CH(C$_6$H$_5$)$_2$ | NH$_2$ | H | |
| 57 | C$_6$H$_4$-(2)-OH | NH$_2$ | H | |
| 58 | C$_6$H$_4$-(3)-OH | NH$_2$ | H | |
| 59 | C$_6$H$_4$-(4)-OH | NH$_2$ | H | |
| 60 | C$_6$H$_4$-(2)-OCH$_3$ | NH$_2$ | H | |
| 61 | C$_6$H$_4$-(3)-OCH$_3$ | NH$_2$ | H | 234 |
| 62 | C$_6$H$_4$-(4)-OCH$_3$ | NH$_2$ | H | 270 |
| 63 | C$_6$H$_4$-(2)-OC$_2$H$_5$ | NH$_2$ | H | |
| 64 | C$_6$H$_4$-(3)-OC$_2$H$_5$ | NH$_2$ | H | |
| 65 | C$_6$H$_4$-(4)-OC$_2$H$_5$ | NH$_2$ | H | |
| 66 | C$_6$H$_4$-(2)-Cl | NH$_2$ | H | |
| 67 | C$_6$H$_4$-(3)-Cl | NH$_2$ | H | |
| 68 | C$_6$H$_4$-(4)-Cl | NH$_2$ | H | |
| 69 | C$_6$H$_4$-(2)-NO$_2$ | NH$_2$ | H | |
| 70 | C$_6$H$_4$-(3)-NO$_2$ | NH$_2$ | H | |
| 71 | C$_6$H$_4$-(4)-NO$_2$ | NH$_2$ | H | |
| 72 | C$_6$H$_4$-(2)-NH$_2$ | NH$_2$ | H | |
| 73 | C$_6$H$_4$-(3)-NH$_2$ | NH$_2$ | H | |
| 74 | C$_6$H$_4$-(4)-NH$_2$ | NH$_2$ | H | |
| 75 | C$_6$H$_4$-(2)-CH$_3$ | NH$_2$ | H | |
| 76 | C$_6$H$_4$-(3)-CH$_3$ | NH$_2$ | H | |
| 77 | C$_6$H$_4$-(4)-CH$_3$ | NH$_2$ | H | |
| 78 | C$_6$H$_4$-(2)-C$_2$H$_5$ | NH$_2$ | H | |
| 79 | C$_6$H$_4$-(3)-C$_2$H$_5$ | NH$_2$ | H | |
| 80 | C$_6$H$_4$-(4)-C$_2$H$_5$ | NH$_2$ | H | |
| 81 | C$_6$H$_4$-(2)-CN | NH$_2$ | H | |
| 82 | C$_6$H$_4$-(3)-CN | NH$_2$ | H | |

TABLE 1-continued

Structure: 3-oxo-4-cyano-pyrazoline with substituents L¹ (on N), L² (on C adjacent to N), L³ (on CH)

| Example No. | L¹ | L² | L³ | Melting point [°C.] |
|---|---|---|---|---|
| 83 | C₆H₄-(4)-CN | NH₂ | H | |
| 84 | C₆H₄-(2)-COOCH₃ | NH₂ | H | |
| 85 | C₆H₄-(3)-COOCH₃ | NH₂ | H | |
| 86 | C₆H₄-(4)-COOCH₃ | NH₂ | H | |
| 87 | Pyrid-2-yl | NH₂ | H | |
| 88 | Pyrid-3-yl | NH₂ | H | 300 |
| 89 | Pyrid-4-yl | NH₂ | H | |
| 90 | (CH₂)₂—C₆H₃-(3)-Cl(2)-CH₃ | NH₂ | H | 270 |
| 91 | (CH₂)₂—C₆H₃-(3,4)-(OCH₃)₂ | NH₂ | H | 220-225 |
| 92 | (CH₂)₂—C₆H₄-(2)-Cl | NH₂ | H | above 270 |
| 93 | C₆H₃-(3,4)-Cl₂ | NH₂ | H | above 270 |
| 94 | CH₂—COOCH₃ | NH₂ | H | above 270 |
| 95 | CH₂—COOC₂H₅ | NH₂ | H | |
| 96 | NH₂ | NH₂ | H | 280-285 |
| 97 | N(CH₃)₂ | NH₂ | H | |
| 98 | N(C₂H₅)₂ | NH₂ | H | |
| 99 | H | N(CH₃)₂ | H | 228-235 |
| 100 | H | N(C₂H₅)₂ | H | 119-123 |
| 101 | H | N(n-C₃H₇)₂ | H | |
| 102 | H | N(n-C₄H₉)₂ | H | |
| 103 | H | pyrrolidin-1-yl | H | 245-249 |
| 104 | H | piperidin-1-yl | H | 267-269 |
| 105 | H | azepan-1-yl | H | |
| 106 | H | morpholin-4-yl | H | 280-284 |
| 107 | H | thiomorpholin-4-yl | H | |
| 108 | H | 4-methylpiperazin-1-yl | H | |
| 109 | CH₃ | NH₂ | CH₃ | 298 |
| 110 | C₂H₅ | NH₂ | CH₃ | |
| 111 | iso-C₃H₇ | NH₂ | CH₃ | |
| 112 | CH₂CH=CH₂ | NH₂ | CH₃ | |
| 113 | Cyclo-C₆H₁₁ | NH₂ | CH₃ | |
| 114 | CH₂CH₂OH | NH₂ | CH₃ | |
| 115 | CH₂CH₂OCH₃ | NH₂ | CH₃ | |
| 116 | CH₂C₆H₅ | NH₂ | CH₃ | |
| 117 | C₆H₅ | NH₂ | CH₃ | |
| 118 | C₆H₄-(4)-OCH₃ | NH₂ | CH₃ | |
| 119 | C₆H₄-(2)-CH₃ | NH₂ | CH₃ | |
| 120 | Pyrid-3-yl | NH₂ | CH₃ | |
| 121 | NH₂ | NH₂ | CH₃ | |
| 122 | H | N(CH₃)₂ | CH₃ | |
| 123 | H | N(C₂H₅)₂ | CH₃ | |

TABLE 1-continued

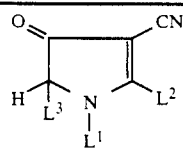

| Example No. | L¹ | L² | L³ | Melting point [°C.] |
|---|---|---|---|---|
| 124 | H | (piperidinyl) | $CH_3$ | |
| 125 | H | (morpholinyl) | $CH_3$ | |
| 126 | $CH_3$ | $NH_2$ | $C_6H_5$ | |
| 127 | $C_2H_5$ | $NH_2$ | $C_6H_5$ | |
| 128 | iso-$C_3H_7$ | $NH_2$ | $C_6H_5$ | |
| 129 | $CH_2CH=CH_2$ | $NH_2$ | $C_6H_5$ | |
| 130 | $CH_2CH_2OH$ | $NH_2$ | $C_6H_5$ | |
| 131 | $CH_2CH_2OCH_3$ | $NH_2$ | $C_6H_5$ | |
| 132 | $CH_2C_6H_5$ | $NH_2$ | $C_6H_5$ | |
| 133 | $C_6H_5$ | $NH_2$ | $C_6H_5$ | |
| 134 | $C_6H_4$-(4)-$OCH_3$ | $NH_2$ | $C_6H_5$ | |
| 135 | $C_6H_4$-(4)-CN | $NH_2$ | $C_6H_5$ | |
| 136 | $NH_2$ | $NH_2$ | $C_6H_5$ | |
| 137 | H | $N(CH_3)_2$ | $C_6H_5$ | |
| 138 | H | $N(C_2H_5)_2$ | $C_6H_5$ | |
| 139 | H | (piperidinyl) | $C_6H_5$ | |
| 140 | H | (morpholinyl) | $C_6H_5$ | |
| 141 | $(CH_2)_3-O-CH_2C_6H_5$ | $NH_2$ | H | 149 |
| 142 | $(CH_2)_3-O-(CH_2)_2-O-C_6H_5$ | $NH_2$ | H | 132 |

EXAMPLE 143

4-Chloro-3-cyano-2-dimethylformamidino-5-formyl-1-methylpyrrole 364 ml of phosphoryl chloride ($POCl_3$) were added dropwise at 0° to 5° C. to 1.5 l of DMF. After one hour at 0° to 5° C., a solution of 137 g of 2-amino-3-cyano-1-methylpyrrolin-4-one (Example 1) in 1.5 l of DMF was added dropwise to the reaction mixture (exothermic reaction with temperature rising to 40° C.). After the mixture had been stirred at 100° C. for 4 hours, it was cooled to room temperature, hydrolyzed with 5 l of water and adjusted to pH 8 to 9 with 50% concentrated sodium hydroxide solution. The beige-colored precipitate was filtered off with suction and dried in an oven at 50° C. 180 g (75% of theory) of the compound of the formula

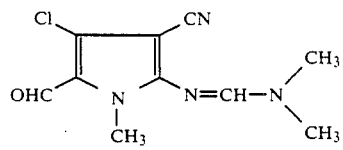

of melting point 150° to 152° C. were obtained. The IR, NMR, UV and mass spectra and the elemental analysis are consistent with the structural formula.

EXAMPLE 144

4-Bromo-3-cyano-2-dimethylformamidino-5-formyl-1-methylpyrrole 172 g of phosphoryl bromide ($POBr_3$) were added dropwise at 0° to 10° C. to 200 ml of DMF. The mixture was stirred for 5 minutes and then a further 100 ml of DMF were added. 27.4 g of 2-amino-3-cyano-1-methylpyrrolin-4-one (Example 1) were introduced a little at a time into the cooled mixture. After the exothermic reaction had subsided, the reaction solution was stirred at 70° C. for 2 hours and then poured into 2 kg of ice-water. The suspension was stirred at room temperature for 8 hours. The precipitate was then filtered off with suction, washed and dried in an oven at 50° C. 12.6 g (22%) of the compound of the formula

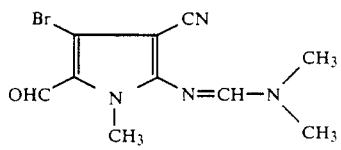

of melting point 180° to 184° C. were obtained. The IR, NMR, UV and mass spectra and the elemental analysis are consistent with the structural formula.

The compounds listed in Table 2 are obtained in a similar manner.

TABLE 2

| Example No. | $L^1$ | $L^2$ | $L^3$ | Melting point [°C.] |
|---|---|---|---|---|
| 145 | $C_2H_5$ | Cl | CHO | |
| 146 | $n-C_3H_7$ | Cl | CHO | |
| 147 | $iso-C_3H_7$ | Cl | CHO | 136–139 |
| 148 | $n-C_4H_9$ | Cl | CHO | |
| 149 | $iso-C_4H_9$ | Cl | CHO | |
| 150 | $sec-C_4H_9$ | Cl | CHO | |
| 151 | $n-C_5H_{11}$ | Cl | CHO | |
| 152 | $Neo-C_5H_{11}$ | Cl | CHO | |
| 153 | $n-C_6H_{13}$ | Cl | CHO | |
| 154 | $n-C_7H_{15}$ | Cl | CHO | |
| 155 | $n-C_8H_{17}$ | Cl | CHO | |
| 156 | $n-C_9H_{19}$ | Cl | CHO | |
| 157 | $n-C_{10}H_{21}$ | Cl | CHO | |
| 158 | $n-C_{11}H_{23}$ | Cl | CHO | |
| 159 | $n-C_{12}H_{25}$ | Cl | CHO | |
| 160 | $n-C_{13}H_{27}$ | Cl | CHO | |
| 161 | $n-C_{14}H_{29}$ | Cl | CHO | |
| 162 | $n-C_{15}H_{31}$ | Cl | CHO | |
| 163 | $n-C_{16}H_{33}$ | Cl | CHO | |
| 164 | $n-C_{17}H_{35}$ | Cl | CHO | |
| 165 | $n-C_{18}H_{37}$ | Cl | CHO | |
| 166 | $n-C_{19}H_{39}$ | Cl | CHO | |
| 167 | $n-C_{20}H_{41}$ | Cl | CHO | |
| 168 | $Cyclo-C_3H_5$ | Cl | CHO | |
| 169 | $Cyclo-C_4H_7$ | Cl | CHO | |
| 170 | $Cyclo-C_5H_9$ | Cl | CHO | |
| 171 | $Cyclo-C_6H_{11}$ | Cl | CHO | |
| 172 | $Cyclo-C_7H_{13}$ | Cl | CHO | |
| 173 | $Cyclo-C_8H_{15}$ | Cl | CHO | |
| 174 | $Cyclo-C_9H_{17}$ | Cl | CHO | |
| 175 | $Cyclo-C_{10}H_{19}$ | Cl | CHO | |
| 176 | $CH_2CH_2Cl$ | Cl | CHO | 119–123 |
| 177 | $CH_2CH_2OCH_3$ | Cl | CHO | |
| 178 | $CH_2CH_2OC_2H_5$ | Cl | CHO | |
| 179 | $CH_2CH_2N=CH-N(CH_3)_2$ | Cl | CHO | |
| 180 | $CH_2CH_2N(CH_3)_2$ | Cl | CHO | |
| 181 | $CH_2CH_2N(C_2H_5)_2$ | Cl | CHO | |
| 182 | $CH_2CH_2SCH_3$ | Cl | CHO | |
| 183 | $CH_2CH_2SC_2H_5$ | Cl | CHO | |
| 184 | $(CH_2)_3Cl$ | Cl | CHO | |
| 185 | $(CH_2)_3OCH_3$ | Cl | CHO | |
| 186 | $(CH_2)_3OC_2H_5$ | Cl | CHO | |
| 187 | $(CH_2)_3N=CH-N(CH_3)_2$ | Cl | CHO | |
| 188 | $(CH_2)_3N(CH_3)_2$ | Cl | CHO | |
| 189 | $(CH_2)_3N(C_2H_5)_2$ | Cl | CHO | |
| 190 | $(CH_2)_3SCH_3$ | Cl | CHO | |
| 191 | $(CH_2)_3SC_2H_5$ | Cl | CHO | |
| 192 | $CH_2C_6H_5$ | Cl | CHO | |
| 193 | $CH_2CH_2C_6H_5$ | Cl | CHO | |
| 194 | $CH(CH_3)C_6H_5$ | Cl | CHO | |
| 195 | $CH(C_6H_5)_2$ | Cl | CHO | |
| 196 | $C_6H_5$ | Cl | CHO | 175–176 |
| 197 | $C_6H_4-(2)-Cl$ | Cl | CHO | |
| 198 | $C_6H_4-(3)-Cl$ | Cl | CHO | |
| 199 | $C_6H_4-(4)-Cl$ | Cl | CHO | |
| 200 | $C_6H_4-(2)-OCH_3$ | Cl | CHO | |
| 201 | $C_6H_4-(3)-OCH_3$ | Cl | CHO | 123–130 |
| 202 | $C_6H_4-(4)-OCH_3$ | Cl | CHO | 140–146 |
| 203 | $C_6H_4-(2)-OC_2H_5$ | Cl | CHO | |
| 204 | $C_6H_4-(3)-OC_2H_5$ | Cl | CHO | |
| 205 | $C_6H_4-(4)-OC_2H_5$ | Cl | CHO | |
| 206 | $C_6H_4-(2)-NO_2$ | Cl | CHO | |
| 207 | $C_6H_4-(3)-NO_2$ | Cl | CHO | |
| 208 | $C_6H_4-(4)-NO_2$ | Cl | CHO | |
| 209 | $CH_2-COOCH_3$ | Cl | CHO | |
| 210 | $CH_2-COOC_2H_5$ | Cl | CHO | |
| 211 | $N=CH-N(CH_3)_2$ | Cl | CHO | 183 |
| 212 | $N(CH_3)_2$ | Cl | CHO | |
| 213 | $N(C_2H_5)_2$ | Cl | CHO | |
| 214 | $C_2H_5$ | Br | CHO | |
| 215 | $n-C_3H_7$ | Br | CHO | |
| 216 | $iso-C_3H_7$ | Br | CHO | |
| 217 | $n-C_4H_9$ | Br | CHO | |
| 218 | $n-C_{13}H_{27}$ | Br | CHO | |
| 219 | $Cyclo-C_6H_{11}$ | Br | CHO | |
| 220 | $C_6H_5$ | Br | CHO | |
| 221 | $C_2H_4Br$ | Br | CHO | |
| 222 | $N=CH-N(CH_3)_2$ | Br | CHO | |
| 223 | $N(CH_3)_2$ | Br | CHO | |
| 224 | $N(C_2H_5)_2$ | Br | CHO | |
| 225 | $CH_3$ | Cl | $CH_3$ | |
| 226 | $C_2H_5$ | Cl | $CH_3$ | |
| 227 | $iso-C_3H_7$ | Cl | $CH_3$ | |
| 228 | $CH_2CH=CH_2$ | Cl | $CH_3$ | |
| 229 | $Cyclo-C_6H_{11}$ | Cl | $CH_3$ | |
| 230 | $CH_2CH_2Cl$ | Cl | $CH_3$ | |
| 231 | $CH_2CH_2OCH_3$ | Cl | $CH_3$ | |
| 232 | $CH_2C_6H_5$ | Cl | $CH_3$ | |
| 233 | $C_6H_5$ | Cl | $CH_3$ | |
| 234 | Pyrid-3-yl | Cl | $CH_3$ | |
| 235 | $CH_3$ | Br | $CH_3$ | |
| 236 | $C_2H_5$ | Br | $CH_3$ | |
| 237 | $iso-C_3H_7$ | Br | $CH_3$ | |
| 238 | $CH_2CH=CH_2$ | Br | $CH_3$ | |
| 239 | $Cyclo-C_6H_{11}$ | Br | $CH_3$ | |
| 240 | $CH_2CH_2Br$ | Br | $CH_3$ | |
| 241 | $CH_2CH_2OCH_3$ | Br | $CH_3$ | |
| 242 | $CH_2C_6H_5$ | Br | $CH_3$ | |
| 243 | $C_6H_5$ | Br | $CH_3$ | |
| 244 | Pyrid-3-yl | Br | $CH_3$ | |
| 245 | $CH_3$ | Cl | $C_6H_5$ | |
| 246 | $C_2H_5$ | Cl | $C_6H_5$ | |
| 247 | $iso-C_3H_7$ | Cl | $C_6H_5$ | |
| 248 | $CH_2CH=CH_2$ | Cl | $C_6H_5$ | |
| 249 | $Cyclo-C_6H_{11}$ | Cl | $C_6H_5$ | |
| 250 | $CH_2CH_2Cl$ | Cl | $C_6H_5$ | |
| 251 | $CH_2CH_2OCH_3$ | Cl | $C_6H_5$ | |
| 252 | $CH_2C_6H_5$ | Cl | $C_6H_5$ | |
| 253 | $C_6H_5$ | Cl | $C_6H_5$ | |
| 254 | Pyrid-3-yl | Cl | $C_6H_5$ | |
| 255 | $CH_3$ | Br | $C_6H_5$ | |
| 256 | $C_2H_5$ | Br | $C_6H_5$ | |
| 257 | $iso-C_3H_7$ | Br | $C_6H_5$ | |
| 258 | $CH_2CH=CH_2$ | Br | $C_6H_5$ | |
| 259 | $Cyclo-C_6H_{11}$ | Br | $C_6H_5$ | |
| 260 | $CH_2CH_2Br$ | Br | $C_6H_5$ | |
| 261 | $CH_2CH_2OCH_3$ | Br | $C_6H_5$ | |
| 262 | $CH_2C_6H_5$ | Br | $C_6H_5$ | |
| 263 | $C_6H_5$ | Br | $C_6H_5$ | |
| 264 | Pyrid-3-yl | Br | $C_6H_5$ | |

EXAMPLE 265

4-Chloro-3-cyano-2-dimethylformamidino-1-methyl-pyrrole 33 ml of phosphoryl chloride (POCl₃) were added dropwise at 0° to 5° C. to 285 ml of DMF. After 1 hour at 0° to 5° C., 41.1 g of 2-amino-3-cyano-1-methylpyrrolin-4-one (Example 1) were added a little at a time to the reaction solution (exothermic reaction with temperature rising to 40° C.). After the mixture had been stirred at 70° C. for 1 hour it was cooled to room temperature, hydrolyzed with 1.5 l of water and adjusted to pH 7 with 240 g of sodium acetate. The precipitate was filtered off with suction and dried in an oven at 50° C. 40.5 g (75% of theory) of the compound of the formula

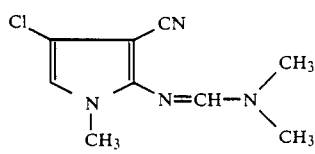

of melting point 88° C. were obtained. The IR, NMR, UV and mass spectra and the elemental analysis are consistent with the structural formula.

EXAMPLE 266

4-Bromo-3-cyano-2-dimethylformamidino-1-methyl-pyrrole 70 g of phosphoryl bromide (POBr₃) were added dropwise at 0° to 10° C. to 190 ml of DMF. After one hour at 0° to 5° C., 27 g of 2-amino-3-cyano-1-methylpyrrolin-4-one (Example 1) were added a little at a time to the reaction solution (exothermic reaction with temperature rising to 30° C.). After the mixture had been stirred at 80° C. for 1 hour it was cooled to room temperature, hydrolyzed with 1.5 l of water and adjusted to pH 7 with 160 g of sodium acetate. The precipitate was filtered off with suction and dried in an oven at 50° C. 22.5 g (44% of theory) of the compound of the formula

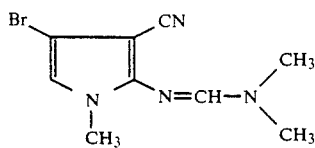

were obtained. The IR, NMR, UV and mass spectra and the elemental analysis are consistent with the structural formula.

The compounds listed in the following Table 3 are obtained in a similar manner.

TABLE 3

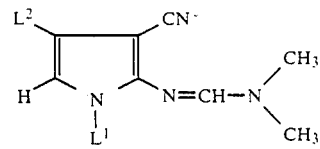

| Example No. | L¹ | L² | Melting point [°C.] |
|---|---|---|---|
| 267 | C₂H₅ | Cl | |
| 268 | n-C₃H₇ | Cl | |
| 269 | iso-C₃H₇ | Cl | |
| 270 | n-C₄H₉ | Cl | |

TABLE 3-continued

| Example No. | L¹ | L² | Melting point [°C.] |
|---|---|---|---|
| 271 | iso-C₄H₉ | Cl | |
| 272 | sec-C₄H₉ | Cl | |
| 273 | n-C₅H₁₁ | Cl | |
| 274 | Neo-C₅H₁₁ | Cl | |
| 275 | n-C₆H₁₃ | Cl | |
| 276 | n-C₇H₁₅ | Cl | |
| 277 | n-C₈H₁₇ | Cl | |
| 278 | n-C₉H₁₉ | Cl | |
| 279 | n-C₁₀H₂₁ | Cl | |
| 280 | n-C₁₁H₂₃ | Cl | |
| 281 | n-C₁₂H₂₅ | Cl | |
| 282 | n-C₁₃H₂₇ | Cl | |
| 283 | n-C₁₄H₂₉ | Cl | |
| 284 | n-C₁₅H₃₁ | Cl | |
| 285 | n-C₁₆H₃₃ | Cl | |
| 286 | n-C₁₇H₃₅ | Cl | |
| 287 | n-C₁₈H₃₇ | Cl | |
| 288 | n-C₁₉H₃₉ | Cl | |
| 289 | n-C₂₀H₄₁ | Cl | |
| 290 | Cyclo-C₃H₅ | Cl | |
| 291 | Cyclo-C₄H₇ | Cl | |
| 292 | Cyclo-C₅H₉ | Cl | |
| 293 | Cyclo-C₆H₁₁ | Cl | |
| 294 | Cyclo-C₇H₁₃ | Cl | |
| 295 | Cyclo-C₈H₁₅ | Cl | |
| 296 | Cyclo-C₉H₁₇ | Cl | |
| 297 | Cyclo-C₁₀H₁₉ | Cl | |
| 298 | CH₂CH₂Cl | Cl | |
| 299 | CH₂CH₂OCH₃ | Cl | |
| 300 | CH₂CH₂OC₂H₅ | Cl | |
| 301 | CH₂CH₂N=CH—N(CH₃)₂ | Cl | |
| 302 | CH₂CH₂N(CH₃)₂ | Cl | |
| 303 | CH₂CH₂N(C₂H₅)₂ | Cl | |
| 304 | CH₂CH₂SCH₃ | Cl | |
| 305 | CH₂CH₂SC₂H₅ | Cl | |
| 306 | (CH₂)₃Cl | Cl | |
| 307 | (CH₂)₃OCH₃ | Cl | |
| 308 | (CH₂)₃OC₂H₅ | Cl | |
| 309 | (CH₂)₃N=CH—N(CH₃)₂ | Cl | |
| 310 | (CH₂)₃N(CH₃)₂ | Cl | |
| 311 | (CH₂)₃N(C₂H₅)₂ | Cl | |
| 312 | (CH₂)₃SCH₃ | Cl | |
| 313 | (CH₂)₃SC₂H₅ | Cl | |
| 314 | CH₂C₆H₅ | Cl | |
| 315 | CH₂CH₂C₆H₅ | Cl | |
| 316 | CH(CH₃)C₆H₅ | Cl | |
| 317 | CH(C₆H₅)₂ | Cl | |
| 318 | C₆H₅ | Cl | |
| 319 | C₆H₄-(2)-Cl | Cl | |
| 320 | C₆H₄-(3)-Cl | Cl | |
| 321 | C₆H₄-(4)-Cl | Cl | |
| 322 | C₆H₄-(2)-OCH₃ | Cl | |
| 323 | C₆H₄-(3)-OCH₃ | Cl | |
| 324 | C₆H₄-(4)-OCH₃ | Cl | |
| 325 | C₆H₄-(2)-OC₂H₅ | Cl | |
| 326 | C₆H₄-(3)-OC₂H₅ | Cl | |
| 327 | C₆H₄-(4)-OC₂H₅ | Cl | |
| 328 | C₆H₄-(2)-NO₂ | Cl | |
| 329 | C₆H₄-(3)-NO₂ | Cl | |
| 330 | C₆H₄-(4)-NO₂ | Cl | |
| 331 | CH₂—COOCH₃ | Cl | |
| 332 | CH₂—COOC₂H₅ | Cl | |
| 333 | N=CH—N(CH₃)₂ | Cl | |
| 334 | N(CH₃)₂ | Cl | |
| 335 | N(C₂H₅)₂ | Cl | |
| 336 | C₂H₅ | Br | |
| 337 | iso-C₃H₇ | Br | |
| 338 | Cyclo-C₆H₁₁ | Br | |
| 339 | CH₂CH₂Br | Br | |
| 340 | CH₂C₆H₅ | Br | |
| 341 | C₆H₅ | Br | |
| 342 | N=CH—N(CH₃)₂ | Br | |

TABLE 3-continued

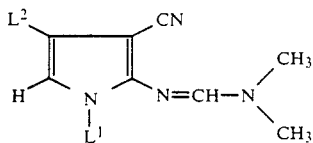

| Example No. | L¹ | L² | Melting point [°C.] |
|---|---|---|---|
| 343 | N(CH₃)₂ | Br | |
| 344 | N(C₂H₅)₂ | Br | |

EXAMPLE 345

2-Amino-4-chloro-3-cyano-5-formyl-1-methylpyrrole 84.8 g of 4-chloro-3-cyano-2-dimethylformamidino-5-formyl-1-methylpyrrole (Example 143) were dissolved in 50 ml of water and 150 ml of ethanol. To this was added a solution of 15 g of KOH in 150 ml of ethanol, and the mixture was refluxed for 10 minutes. It was then poured into 1 kg of ice-water, the pH was adjusted to 7 with concentrated formic acid, and the precipitate was filtered off with suction, washed and dried in an oven at 50° C. 60.2 g (92% of theory) of the compound of the formula

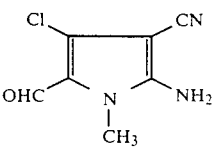

of melting point 282° to 285° C. are obtained. The IR, NMR, UV and mass spectra and the elemental analysis are consistent with the structural formula.

The compounds listed in Table 4 are obtained in a similar manner to Example 345.

TABLE 4

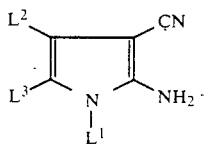

| Example No. | L¹ | L² | L³ | Melting point [°C.] |
|---|---|---|---|---|
| 346 | C₂H₅ | Cl | CHO | |
| 347 | n-C₃H₇ | Cl | CHO | |
| 348 | iso-C₃H₇ | Cl | CHO | 180–195 |
| 349 | n-C₄H₉ | Cl | CHO | |
| 350 | iso-C₄H₉ | Cl | CHO | |
| 351 | sec-C₄H₉ | Cl | CHO | |
| 352 | n-C₅H₁₁ | Cl | CHO | |
| 353 | Neo-C₅H₁₁ | Cl | CHO | |
| 354 | n-C₆H₁₃ | Cl | CHO | |
| 355 | n-C₇H₁₅ | Cl | CHO | |
| 356 | n-C₈H₁₇ | Cl | CHO | |
| 357 | n-C₉H₁₉ | Cl | CHO | |
| 358 | n-C₁₀H₂₁ | Cl | CHO | |
| 359 | n-C₁₁H₂₃ | Cl | CHO | |
| 360 | n-C₁₂H₂₅ | Cl | CHO | |
| 361 | n-C₁₃H₂₇ | Cl | CHO | |
| 362 | n-C₁₄H₂₉ | Cl | CHO | |
| 363 | n-C₁₅H₃₁ | Cl | CHO | |
| 364 | n-C₁₆H₃₃ | Cl | CHO | |
| 365 | n-C₁₇H₃₅ | Cl | CHO | |
| 366 | n-C₁₈H₃₇ | Cl | CHO | |
| 367 | n-C₁₉H₃₉ | Cl | CHO | |
| 368 | n-C₂₀H₄₁ | Cl | CHO | |

TABLE 4-continued

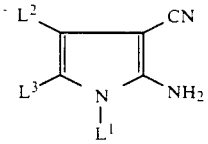

| Example No. | L¹ | L² | L³ | Melting point [°C.] |
|---|---|---|---|---|
| 369 | Cyclo-C₃H₅ | Cl | CHO | |
| 370 | Cyclo-C₄H₇ | Cl | CHO | |
| 371 | Cyclo-C₅H₉ | Cl | CHO | |
| 372 | Cyclo-C₆H₁₁ | Cl | CHO | |
| 373 | Cyclo-C₇H₁₃ | Cl | CHO | |
| 374 | Cyclo-C₈H₁₅ | Cl | CHO | |
| 375 | Cyclo-C₉H₁₇ | Cl | CHO | |
| 376 | Cyclo-C₁₀H₁₉ | Cl | CHO | |
| 377 | CH₂CH₂Cl | Cl | CHO | |
| 378 | CH₂CH₂OCH₃ | Cl | CHO | |
| 379 | CH₂CH₂OC₂H₅ | Cl | CHO | |
| 380 | CH₂CH₂NH₂ | Cl | CHO | |
| 381 | CH₂CH₂N(CH₃)₂ | Cl | CHO | |
| 382 | CH₂CH₂N(C₂H₅)₂ | Cl | CHO | |
| 383 | CH₂CH₂SCH₃ | Cl | CHO | |
| 384 | CH₂CH₂SC₂H₅ | Cl | CHO | |
| 385 | (CH₂)₃Cl | Cl | CHO | |
| 386 | (CH₂)₃OCH₃ | Cl | CHO | |
| 387 | (CH₂)₃OC₂H₅ | Cl | CHO | |
| 388 | (CH₂)₃NH₂ | Cl | CHO | |
| 389 | (CH₂)₃N(CH₃)₂ | Cl | CHO | |
| 390 | (CH₂)₃N(C₂H₅)₂ | Cl | CHO | |
| 391 | (CH₂)₃SCH₃ | Cl | CHO | |
| 392 | (CH₂)₃SC₂H₅ | Cl | CHO | |
| 393 | CH₂C₆H₅ | Cl | CHO | |
| 394 | CH₂CH₂C₆H₅ | Cl | CHO | |
| 395 | CH(CH₃)C₆H₅ | Cl | CHO | |
| 396 | CH(C₆H₅)₂ | Cl | CHO | |
| 397 | C₆H₅ | Cl | CHO | 220–226 |
| 398 | C₆H₄-(2)-Cl | Cl | CHO | |
| 399 | C₆H₄-(3)-Cl | Cl | CHO | |
| 400 | C₆H₄-(4)-Cl | Cl | CHO | |
| 401 | C₆H₄-(2)-OCH₃ | Cl | CHO | |
| 402 | C₆H₄-(3)-OCH₃ | Cl | CHO | 123–130 |
| 403 | C₆H₄-(4)-OCH₃ | Cl | CHO | 140–146 |
| 404 | C₆H₄-(2)-OC₂H₅ | Cl | CHO | |
| 405 | C₆H₄-(3)-OC₂H₅ | Cl | CHO | |
| 406 | C₆H₄-(4)-OC₂H₅ | Cl | CHO | |
| 407 | C₆H₄-(2)-NO₂ | Cl | CHO | |
| 408 | C₆H₄-(3)-NO₂ | Cl | CHO | |
| 409 | C₆H₄-(4)-NO₂ | Cl | CHO | |
| 410 | CH₂—COOCH₃ | Cl | CHO | |
| 411 | CH₂—COOC₂H₅ | Cl | CHO | |
| 412 | NH₂ | Cl | CHO | |
| 413 | N(CH₃)₂ | Cl | CHO | |
| 414 | N(C₂H₅)₂ | Cl | CHO | |
| 415 | CH₃ | Br | CHO | |
| 416 | C₂H₅ | Br | CHO | |
| 417 | n-C₃H₇ | Br | CHO | |
| 418 | iso-C₃H₇ | Br | CHO | |
| 419 | n-C₄H₉ | Br | CHO | |
| 420 | n-C₁₃H₁₇ | Br | CHO | |
| 421 | Cyclo-C₆H₁₁ | Br | CHO | |
| 422 | C₆H₅ | Br | CHO | |
| 423 | C₂H₄Br | Br | CHO | |
| 424 | NH₂ | Br | CHO | |
| 425 | N(CH₃)₂ | Br | CHO | |
| 426 | N(C₂H₅)₂ | Br | CHO | |
| 427 | CH₃ | Cl | CH₃ | |
| 428 | C₂H₅ | Cl | CH₃ | |
| 429 | n-C₃H₇ | Cl | CH₃ | |
| 430 | iso-C₃H₇ | Cl | CH₃ | |
| 431 | n-C₄H₉ | Cl | CH₃ | |
| 432 | n-C₁₃H₁₇ | Cl | CH₃ | |
| 433 | Cyclo-C₆H₁₁ | Cl | CH₃ | |
| 434 | C₆H₅ | Cl | CH₃ | |
| 435 | C₂H₄Br | Cl | CH₃ | |
| 436 | NH₂ | Cl | CH₃ | |
| 437 | N(CH₃)₂ | Cl | CH₃ | |
| 438 | N(C₂H₅)₂ | Cl | CH₃ | |
| 439 | CH₃ | Br | CH₃ | |
| 440 | C₂H₅ | Br | CH₃ | |

TABLE 4-continued

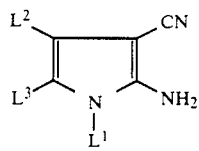

| Example No. | L¹ | L² | L³ | Melting point [°C.] |
|---|---|---|---|---|
| 441 | n-$C_3H_7$ | Br | $CH_3$ | |
| 442 | iso-$C_3H_7$ | Br | $CH_3$ | |
| 443 | n-$C_4H_9$ | Br | $CH_3$ | |
| 444 | n-$C_{13}H_{17}$ | Br | $CH_3$ | |
| 445 | Cyclo-$C_6H_{11}$ | Br | $CH_3$ | |
| 446 | $C_6H_5$ | Br | $CH_3$ | |
| 447 | $C_2H_4Br$ | Br | $CH_3$ | |
| 448 | $NH_2$ | Br | $CH_3$ | |
| 449 | $N(CH_3)_2$ | Br | $CH_3$ | |
| 450 | $N(C_2H_5)_2$ | Br | $CH_3$ | |
| 451 | $CH_3$ | Cl | $C_6H_5$ | |
| 452 | $C_2H_5$ | Cl | $C_6H_5$ | |
| 453 | n-$C_3H_7$ | Cl | $C_6H_5$ | |
| 454 | iso-$C_3H_7$ | Cl | $C_6H_5$ | |
| 455 | n-$C_4H_9$ | Cl | $C_6H_5$ | |
| 456 | n-$C_{13}H_{17}$ | Cl | $C_6H_5$ | |
| 457 | Cyclo-$C_6H_{11}$ | Cl | $C_6H_5$ | |
| 458 | $C_6H_5$ | Cl | $C_6H_5$ | |
| 459 | $C_2H_4Br$ | Cl | $C_6H_5$ | |
| 460 | $NH_2$ | Cl | $C_6H_5$ | |
| 461 | $N(CH_3)_2$ | Cl | $C_6H_5$ | |
| 462 | $N(C_2H_5)_2$ | Cl | $C_6H_5$ | |
| 463 | $CH_3$ | Br | $C_6H_5$ | |
| 464 | $C_2H_5$ | Br | $C_6H_5$ | |
| 465 | n-$C_3H_7$ | Br | $C_6H_5$ | |
| 466 | iso-$C_3H_7$ | Br | $C_6H_5$ | |
| 467 | n-$C_4H_9$ | Br | $C_6H_5$ | |
| 468 | n-$C_{13}H_{17}$ | Br | $C_6H_5$ | |
| 469 | Cyclo-$C_6H_{11}$ | Br | $C_6H_5$ | |
| 470 | $C_6H_5$ | Br | $C_6H_5$ | |
| 471 | $C_2H_4Br$ | Br | $C_6H_5$ | |
| 472 | $NH_2$ | Br | $C_6H_5$ | |
| 473 | $N(CH_3)_2$ | Br | $C_6H_5$ | |
| 474 | $N(C_2H_5)_2$ | Br | $C_6H_5$ | |
| 475 | $CH_3$ | Cl | H | |
| 476 | $C_2H_5$ | Cl | H | |
| 477 | n-$C_3H_7$ | Cl | H | |
| 478 | iso-$C_3H_7$ | Cl | H | |
| 479 | n-$C_4H_9$ | Cl | H | |
| 480 | n-$C_{13}H_{17}$ | Cl | H | |
| 481 | Cyclo-$C_6H_{11}$ | Cl | H | |
| 482 | $C_6H_5$ | Cl | H | |
| 483 | $C_2H_4Br$ | Cl | H | |
| 484 | $NH_2$ | Cl | H | |
| 485 | $N(CH_3)_2$ | Cl | H | |
| 486 | $N(C_2H_5)_2$ | Cl | H | |
| 487 | $CH_3$ | Br | H | |
| 488 | $C_2H_5$ | Br | H | |
| 489 | n-$C_3H_7$ | Br | H | |
| 490 | iso-$C_3H_7$ | Br | H | |
| 491 | n-$C_4H_9$ | Br | H | |
| 492 | n-$C_{13}H_{17}$ | Br | H | |
| 493 | Cyclo-$C_6H_{11}$ | Br | H | |
| 494 | $C_6H_5$ | Br | H | |
| 495 | $C_2H_4Br$ | Br | H | |
| 496 | $NH_2$ | Br | H | |
| 497 | $N(CH_3)_2$ | Br | H | |
| 498 | $N(C_2H_5)_2$ | Br | H | |

EXAMPLE 499

2-Amino-4-chloro-5-formyl-1-methylpyrrole-3-carboxamide 9.54 g of 4-chloro-3-cyano-2-dimethylformamidino-5-formyl-1-methylpyrrole (Example 143) were refluxed in 100 ml of 5% by weight aqueous sodium hydroxide solution for one hour. After cooling, the precipitate was filtered off with suction, washed and dried. 4.00 g (50% of theory) of the compound of the formula

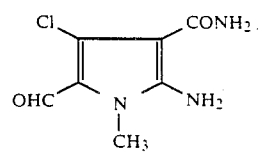

of melting point 217° C. (decomposition) were obtained. The IR, NMR, UV and mass spectra and the elemental analysis are constituent with the structural formula.

The compounds listed in Table 5 are obtained in a similar manner to Example 499.

TABLE 5

| Example No. | L¹ | L² | L³ | Melting point [°C.] |
|---|---|---|---|---|
| 500 | $C_2H_5$ | Cl | CHO | |
| 501 | n-$C_3H_7$ | Cl | CHO | |
| 502 | iso-$C_3H_7$ | Cl | CHO | |
| 503 | n-$C_4H_9$ | Cl | CHO | |
| 504 | iso-$C_4H_9$ | Cl | CHO | |
| 505 | sec-$C_4H_9$ | Cl | CHO | |
| 506 | n-$C_5H_{11}$ | Cl | CHO | |
| 507 | Neo-$C_5H_{11}$ | Cl | CHO | |
| 508 | n-$C_6H_{13}$ | Cl | CHO | |
| 509 | n-$C_7H_{15}$ | Cl | CHO | |
| 510 | n-$C_8H_{17}$ | Cl | CHO | |
| 511 | n-$C_9H_{19}$ | Cl | CHO | |
| 512 | n-$C_{10}H_{21}$ | Cl | CHO | |
| 513 | n-$C_{11}H_{23}$ | Cl | CHO | |
| 514 | n-$C_{12}H_{25}$ | Cl | CHO | |
| 515 | n-$C_{13}H_{27}$ | Cl | CHO | |
| 516 | n-$C_{14}H_{29}$ | Cl | CHO | |
| 517 | n-$C_{15}H_{31}$ | Cl | CHO | |
| 518 | n-$C_{16}H_{33}$ | Cl | CHO | |
| 519 | n-$C_{17}H_{35}$ | Cl | CHO | |
| 520 | n-$C_{18}H_{37}$ | Cl | CHO | |
| 521 | n-$C_{19}H_{39}$ | Cl | CHO | |
| 522 | n-$C_{20}H_{41}$ | Cl | CHO | |
| 523 | Cyclo-$C_3H_5$ | Cl | CHO | |
| 524 | Cyclo-$C_4H_7$ | Cl | CHO | |
| 525 | Cyclo-$C_5H_9$ | Cl | CHO | |
| 526 | Cyclo-$C_6H_{11}$ | Cl | CHO | |
| 527 | Cyclo-$C_7H_{13}$ | Cl | CHO | |
| 528 | Cyclo-$C_8H_{15}$ | Cl | CHO | |
| 529 | Cyclo-$C_9H_{17}$ | Cl | CHO | |
| 530 | Cyclo-$C_{10}H_{19}$ | Cl | CHO | |
| 531 | $CH_2CH_2Cl$ | Cl | CHO | |
| 532 | $CH_2CH_2OCH_3$ | Cl | CHO | |
| 533 | $CH_2CH_2OC_2H_5$ | Cl | CHO | |
| 534 | $CH_2CH_2NH_2$ | Cl | CHO | |
| 535 | $CH_2CH_2N(CH_3)_2$ | Cl | CHO | |
| 536 | $CH_2CH_2N(C_2H_5)_2$ | Cl | CHO | |
| 537 | $CH_2CH_2SCH_3$ | Cl | CHO | |
| 538 | $CH_2CH_2SC_2H_5$ | Cl | CHO | |
| 539 | $(CH_2)_3Cl$ | Cl | CHO | |
| 540 | $(CH_2)_3OCH_3$ | Cl | CHO | |
| 541 | $(CH_2)_3OC_2H_5$ | Cl | CHO | |
| 542 | $(CH_2)_3NH_2$ | Cl | CHO | |
| 543 | $(CH_2)_3N(CH_3)_2$ | Cl | CHO | |
| 544 | $(CH_2)_3N(C_2H_5)_2$ | Cl | CHO | |
| 545 | $(CH_2)_3SCH_3$ | Cl | CHO | |
| 546 | $(CH_2)_3SC_2H_5$ | Cl | CHO | |
| 547 | $CH_2C_6H_5$ | Cl | CHO | |
| 548 | $CH_2CH_2C_6H_5$ | Cl | CHO | |
| 549 | $CH(CH_3)C_6H_5$ | Cl | CHO | |
| 550 | $CH(C_6H_5)_2$ | Cl | CHO | |
| 551 | $C_6H_5$ | Cl | CHO | |
| 552 | $C_6H_4$-(2)-Cl | Cl | CHO | |

TABLE 5-continued

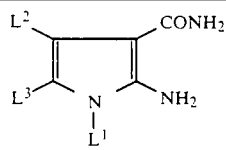

| Example No. | L¹ | L² | L³ | Melting point [°C.] |
|---|---|---|---|---|
| 553 | C₆H₄-(3)-Cl | Cl | CHO | |
| 554 | C₆H₄-(4)-Cl | Cl | CHO | |
| 555 | C₆H₄-(2)-OCH₃ | Cl | CHO | |
| 556 | C₆H₄-(3)-OCH₃ | Cl | CHO | |
| 557 | C₆H₄-(4)-OCH₃ | Cl | CHO | |
| 558 | C₆H₄-(2)-OC₂H₅ | Cl | CHO | |
| 559 | C₆H₄-(3)-OC₂H₅ | Cl | CHO | |
| 560 | C₆H₄-(4)-OC₂H₅ | Cl | CHO | |
| 561 | C₆H₄-(2)-NO₂ | Cl | CHO | |
| 562 | C₆H₄-(3)-NO₂ | Cl | CHO | |
| 563 | C₆H₄-(4)-NO₂ | Cl | CHO | |
| 564 | CH₂—COOCH₃ | Cl | CHO | |
| 565 | CH₂—COOC₂H₅ | Cl | CHO | |
| 566 | NH₂ | Cl | CHO | |
| 567 | N(CH₃)₂ | Cl | CHO | |
| 568 | N(C₂H₅)₂ | Cl | CHO | |
| 569 | CH₃ | Br | CHO | |
| 570 | C₂H₅ | Br | CHO | |
| 571 | n-C₃H₇ | Br | CHO | |
| 572 | iso-C₃H₇ | Br | CHO | |
| 573 | n-C₄H₉ | Br | CHO | |
| 574 | n-C₁₃H₁₇ | Br | CHO | |
| 575 | Cyclo-C₆H₁₁ | Br | CHO | |
| 576 | C₆H₅ | Br | CHO | |
| 577 | C₂H₄Br | Br | CHO | |
| 578 | NH₂ | Br | CHO | |
| 579 | N(CH₃)₂ | Br | CHO | |
| 580 | N(C₂H₅)₂ | Br | CHO | |
| 581 | CH₃ | Cl | CH₃ | |
| 582 | C₂H₅ | Cl | CH₃ | |
| 583 | n-C₃H₇ | Cl | CH₃ | |
| 584 | iso-C₃H₇ | Cl | CH₃ | |
| 585 | n-C₄H₉ | Cl | CH₃ | |
| 586 | n-C₁₃H₁₇ | Cl | CH₃ | |
| 587 | Cyclo-C₆H₁₁ | Cl | CH₃ | |
| 588 | C₆H₅ | Cl | CH₃ | |
| 589 | C₂H₄Cl | Cl | CH₃ | |
| 590 | NH₂ | Cl | CH₃ | |
| 591 | N(CH₃)₂ | Cl | CH₃ | |
| 592 | N(C₂H₅)₂ | Cl | CH₃ | |
| 593 | CH₃ | Br | CH₃ | |
| 594 | C₂H₅ | Br | CH₃ | |
| 595 | n-C₃H₇ | Br | CH₃ | |
| 596 | iso-C₃H₇ | Br | CH₃ | |
| 597 | n-C₄H₉ | Br | CH₃ | |
| 598 | n-C₁₃H₁₇ | Br | CH₃ | |
| 599 | Cyclo-C₆H₁₁ | Br | CH₃ | |
| 600 | C₆H₅ | Br | CH₃ | |
| 601 | C₂H₄Br | Br | CH₃ | |
| 602 | NH₂ | Br | CH₃ | |
| 603 | N(CH₃)₂ | Br | CH₃ | |
| 604 | N(C₂H₅)₂ | Br | CH₃ | |
| 605 | CH₃ | Cl | C₆H₅ | |
| 606 | C₂H₅ | Cl | C₆H₅ | |
| 607 | n-C₃H₇ | Cl | C₆H₅ | |
| 608 | iso-C₃H₇ | Cl | C₆H₅ | |
| 609 | n-C₄H₉ | Cl | C₆H₅ | |
| 610 | n-C₁₃H₁₇ | Cl | C₆H₅ | |
| 611 | Cyclo-C₆H₁₁ | Cl | C₆H₅ | |
| 612 | C₆H₅ | Cl | C₆H₅ | |
| 613 | C₂H₄Cl | Cl | C₆H₅ | |
| 614 | NH₂ | Cl | C₆H₅ | |
| 615 | N(CH₃)₂ | Cl | C₆H₅ | |
| 616 | N(C₂H₅)₂ | Cl | C₆H₅ | |
| 617 | CH₃ | Br | C₆H₅ | |
| 618 | C₂H₅ | Br | C₆H₅ | |
| 619 | n-C₃H₇ | Br | C₆H₅ | |
| 620 | iso-C₃H₇ | Br | C₆H₅ | |
| 621 | n-C₄H₉ | Br | C₆H₅ | |
| 622 | n-C₁₃H₁₇ | Br | C₆H₅ | |
| 623 | Cyclo-C₆H₁₁ | Br | C₆H₅ | |
| 624 | C₆H₅ | Br | C₆H₅ | |

TABLE 5-continued

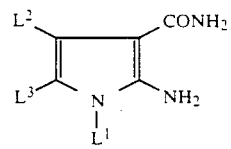

| Example No. | L¹ | L² | L³ | Melting point [°C.] |
|---|---|---|---|---|
| 625 | C₂H₄Br | Br | C₆H₅ | |
| 626 | NH₂ | Br | C₆H₅ | |
| 627 | N(CH₃)₂ | Br | C₆H₅ | |
| 628 | N(C₂H₅)₂ | Br | C₆H₅ | |
| 629 | CH₃ | Cl | H | |
| 630 | C₂H₅ | Cl | H | |
| 631 | n-C₃H₇ | Cl | H | |
| 632 | iso-C₃H₇ | Cl | H | |
| 633 | n-C₄H₉ | Cl | H | |
| 634 | n-C₁₃H₁₇ | Cl | H | |
| 635 | Cyclo-C₆H₁₁ | Cl | H | |
| 636 | C₆H₅ | Cl | H | |
| 637 | C₂H₄OH | Cl | H | |
| 638 | NH₂ | Cl | H | |
| 639 | N(CH₃)₂ | Cl | H | |
| 640 | N(C₂H₅)₂ | Cl | H | |
| 641 | CH₃ | Br | H | |
| 642 | C₂H₅ | Br | H | |
| 643 | n-C₃H₇ | Br | H | |
| 644 | iso-C₃H₇ | Br | H | |
| 645 | n-C₄H₉ | Br | H | |
| 646 | n-C₁₃H₁₇ | Br | H | |
| 647 | Cyclo-C₆H₁₁ | Br | H | |
| 648 | C₆H₅ | Br | H | |
| 649 | C₂H₄Br | Br | H | |
| 650 | NH₂ | Br | H | |
| 651 | N(CH₃)₂ | Br | H | |
| 652 | N(C₂H₅)₂ | Br | H | |

EXAMPLE 653

4-Chloro-3-cyano-2-dimethylformamidino-1-methyl-pyrrole-5-carbaldehyde oxime 7.2 g of 4-chloro-3-cyano-2-dimethylformamidino-5formyl-1-methylpyrrole (Example 143), 4.2 g of hydroxylammonium chloride and 5.1 g of sodium bicarbonate were refluxed in 100 ml of ethanol/water (1:1) for 3 hours. After cooling, 0.5 l of water was added, and the precipitate was filtered off with suction, washed and dried. 5.5 g of the compound of the formula

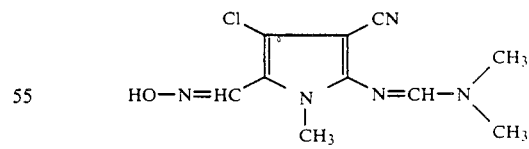

of melting point 220° to 220° C. were obtained. The IR, NMR, UV and mass spectra and the elemental analysis are consistent with the structural formula.

The compounds listed in Table 6 are obtained in a similar manner to Example 653.

TABLE 6

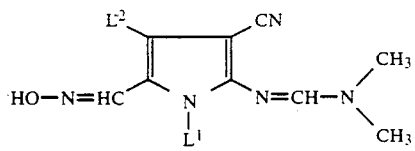

| Example No. | $L^1$ | $L^2$ | Melting point [°C.] |
|---|---|---|---|
| 654 | $C_2H_5$ | Cl | |
| 655 | $n\text{-}C_3H_7$ | Cl | |
| 656 | $iso\text{-}C_3H_7$ | Cl | |
| 657 | $n\text{-}C_4H_9$ | Cl | |
| 658 | $iso\text{-}C_4H_9$ | Cl | |
| 659 | $sec\text{-}C_4H_9$ | Cl | |
| 660 | $n\text{-}C_5H_{11}$ | Cl | |
| 661 | $Neo\text{-}C_5H_{11}$ | Cl | |
| 662 | $n\text{-}C_6H_{13}$ | Cl | |
| 663 | $n\text{-}C_7H_{15}$ | Cl | |
| 664 | $n\text{-}C_8H_{17}$ | Cl | |
| 665 | $n\text{-}C_9H_{19}$ | Cl | |
| 666 | $n\text{-}C_{10}H_{21}$ | Cl | |
| 667 | $n\text{-}C_{11}H_{23}$ | Cl | |
| 668 | $n\text{-}C_{12}H_{25}$ | Cl | |
| 669 | $n\text{-}C_{13}H_{27}$ | Cl | |
| 670 | $n\text{-}C_{14}H_{29}$ | Cl | |
| 671 | $n\text{-}C_{15}H_{31}$ | Cl | |
| 672 | $n\text{-}C_{16}H_{33}$ | Cl | |
| 673 | $n\text{-}C_{17}H_{35}$ | Cl | |
| 674 | $n\text{-}C_{18}H_{37}$ | Cl | |
| 675 | $n\text{-}C_{19}H_{39}$ | Cl | |
| 676 | $n\text{-}C_{20}H_{41}$ | Cl | |
| 677 | $Cyclo\text{-}C_3H_5$ | Cl | |
| 678 | $Cyclo\text{-}C_4H_7$ | Cl | |
| 679 | $Cyclo\text{-}C_5H_9$ | Cl | |
| 680 | $Cyclo\text{-}C_6H_{11}$ | Cl | |
| 681 | $Cyclo\text{-}C_7H_{13}$ | Cl | |
| 682 | $Cyclo\text{-}C_8H_{15}$ | Cl | |
| 683 | $Cyclo\text{-}C_9H_{17}$ | Cl | |
| 684 | $Cyclo\text{-}C_{10}H_{19}$ | Cl | |
| 685 | $CH_2CH_2Cl$ | Cl | |
| 686 | $CH_2CH_2OCH_3$ | Cl | |
| 687 | $CH_2CH_2OC_2H_5$ | Cl | |
| 688 | $CH_2CH_2N=CH-N(CH_3)_2$ | Cl | |
| 689 | $CH_2CH_2N(CH_3)_2$ | Cl | |
| 690 | $CH_2CH_2N(C_2H_5)_2$ | Cl | |
| 691 | $CH_2CH_2SCH_3$ | Cl | |
| 692 | $CH_2CH_2SC_2H_5$ | Cl | |
| 693 | $(CH_2)_3Cl$ | Cl | |
| 694 | $(CH_2)_3OCH_3$ | Cl | |
| 695 | $(CH_2)_3OC_2H_5$ | Cl | |
| 696 | $(CH_2)_3N=CH-N(CH_3)_2$ | Cl | |
| 697 | $(CH_2)_3N(CH_3)_2$ | Cl | |
| 698 | $(CH_2)_3N(C_2H_5)_2$ | Cl | |
| 699 | $(CH_2)_3SCH_3$ | Cl | |
| 700 | $(CH_2)_3SC_2H_5$ | Cl | |
| 701 | $CH_2C_6H_5$ | Cl | |
| 702 | $CH_2CH_2C_6H_5$ | Cl | |
| 703 | $CH(CH_3)C_6H_5$ | Cl | |
| 704 | $CH(C_6H_5)_2$ | Cl | |
| 705 | $C_6H_5$ | Cl | |
| 706 | $C_6H_4\text{-}(2)\text{-}Cl$ | Cl | |
| 707 | $C_6H_4\text{-}(3)\text{-}Cl$ | Cl | |
| 708 | $C_6H_4\text{-}(4)\text{-}Cl$ | Cl | |
| 709 | $C_6H_4\text{-}(2)\text{-}OCH_3$ | Cl | |
| 710 | $C_6H_4\text{-}(3)\text{-}OCH_3$ | Cl | |
| 711 | $C_6H_4\text{-}(4)\text{-}OCH_3$ | Cl | |
| 712 | $C_6H_4\text{-}(2)\text{-}OC_2H_5$ | Cl | |
| 713 | $C_6H_4\text{-}(3)\text{-}OC_2H_5$ | Cl | |
| 714 | $C_6H_4\text{-}(4)\text{-}OC_2H_5$ | Cl | |
| 715 | $C_6H_4\text{-}(2)\text{-}NO_2$ | Cl | |
| 716 | $C_6H_4\text{-}(3)\text{-}NO_2$ | Cl | |
| 717 | $C_6H_4\text{-}(4)\text{-}NO_2$ | Cl | |
| 718 | $CH_2-COOCH_3$ | Cl | |
| 719 | $CH_2-COOC_2H_5$ | Cl | |
| 720 | $N=CH-N(CH_3)_2$ | Cl | |
| 721 | $N(CH_3)_2$ | Cl | |
| 722 | $N(C_2H_5)_2$ | Cl | |
| 723 | $CH_3$ | Br | |
| 724 | $C_2H_5$ | Br | |
| 725 | $n\text{-}C_3H_7$ | Br | |

TABLE 6-continued

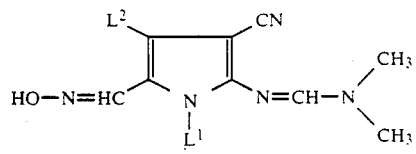

| Example No. | $L^1$ | $L^2$ | Melting point [°C.] |
|---|---|---|---|
| 726 | $iso\text{-}C_3H_7$ | Br | |
| 727 | $CH_2CH_2NH_2$ | Br | |
| 728 | $CH_2CH_2CH_2NH_2$ | Br | |
| 729 | $Cyclo\text{-}C_6H_{11}$ | Br | |
| 730 | $C_6H_5$ | Br | |
| 731 | $C_2H_4Br$ | Br | |
| 732 | $NH_2$ | Br | |
| 733 | $N(CH_3)_2$ | Br | |
| 734 | $N(C_2H_5)_2$ | Br | |

EXAMPLE 735

2-Acetylamino-4-chloro-3,5-dicyano-1-metylpyrrole 5.0 g of 4-chloro-b 3-cyano-2-dimethylformamidino-1-metylpyrrole-5-carbaldehyde oxime (Example 653) were refluxed in 40 ml of acetic anhydride for 15 hours. After addition of 100 ml of water the reaction mixture was refluxed for a further 10 minutes and then poured into 300 g of ice. The mixture was adjusted to pH 5 with 50% concentrated sodium hydroxide solution, and the precipitate was left to stand at room temperature for two hours and then filtered off with suction, washed and dried. 2.2 g (47% of theory) of the compound of the formula

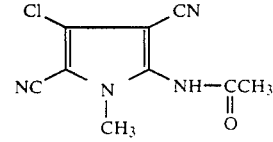

of melting point 180° to 182° C. were obtained. The IR, NMR, UV and mass spectra and the elemental analysis are consistent with the structural formula.

The compounds listed in Table 7 are obtained in a similar manner to Example 735.

TABLE 7

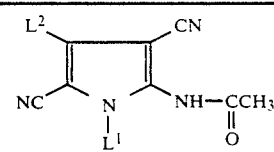

| Example No. | $L^1$ | $L^2$ | Melting point [°C.] |
|---|---|---|---|
| 736 | $C_2H_5$ | Cl | |
| 737 | $n\text{-}C_3H_7$ | Cl | |
| 738 | $iso\text{-}C_3H_7$ | Cl | |
| 739 | $n\text{-}C_4H_9$ | Cl | |
| 740 | $iso\text{-}C_4H_9$ | Cl | |
| 741 | $sec\text{-}C_4H_9$ | Cl | |
| 742 | $n\text{-}C_5H_{11}$ | Cl | |
| 743 | $Neo\text{-}C_5H_{11}$ | Cl | |
| 744 | $n\text{-}C_6H_{13}$ | Cl | |
| 745 | $n\text{-}C_7H_{15}$ | Cl | |
| 746 | $n\text{-}C_8H_{17}$ | Cl | |
| 747 | $n\text{-}C_9H_{19}$ | Cl | |
| 748 | $n\text{-}C_{10}H_{21}$ | Cl | |
| 749 | $n\text{-}C_{11}H_{23}$ | Cl | |
| 750 | $n\text{-}C_{12}H_{25}$ | Cl | |

TABLE 7-continued

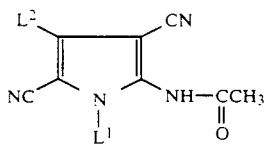

| Example No. | L¹ | L² | Melting point [°C.] |
|---|---|---|---|
| 751 | n-$C_{13}H_{27}$ | Cl | |
| 752 | n-$C_{14}H_{29}$ | Cl | |
| 753 | n-$C_{15}H_{31}$ | Cl | |
| 754 | n-$C_{16}H_{33}$ | Cl | |
| 755 | n-$C_{17}H_{35}$ | Cl | |
| 756 | n-$C_{18}H_{37}$ | Cl | |
| 757 | n-$C_{19}H_{39}$ | Cl | |
| 758 | n-$C_{20}H_{41}$ | Cl | |
| 759 | Cyclo-$C_3H_5$ | Cl | |
| 760 | Cyclo-$C_4H_7$ | Cl | |
| 761 | Cyclo-$C_5H_9$ | Cl | |
| 762 | Cyclo-$C_6H_{11}$ | Cl | |
| 763 | Cyclo-$C_7H_{13}$ | Cl | |
| 764 | Cyclo-$C_8H_{15}$ | Cl | |
| 765 | Cyclo-$C_9H_{17}$ | Cl | |
| 766 | Cyclo-$C_{10}H_{19}$ | Cl | |
| 767 | $CH_2CH_2Cl$ | Cl | |
| 768 | $CH_2CH_2OCH_3$ | Cl | |
| 769 | $CH_2CH_2OC_2H_5$ | Cl | |
| 770 | $CH_2CH_2N=CH-N(CH_3)_2$ | Cl | |
| 771 | $CH_2CH_2N(CH_3)_2$ | Cl | |
| 772 | $CH_2CH_2N(C_2H_5)_2$ | Cl | |
| 773 | $CH_2CH_2SCH_3$ | Cl | |
| 774 | $CH_2CH_2SC_2H_5$ | Cl | |
| 775 | $(CH_2)_3Cl$ | Cl | |
| 776 | $(CH_2)_3OCH_3$ | Cl | |
| 777 | $(CH_2)_3OC_2H_5$ | Cl | |
| 778 | $(CH_2)_3N=CH-N(CH_3)_2$ | Cl | |
| 779 | $(CH_2)_3N(CH_3)_2$ | Cl | |
| 780 | $(CH_2)_3N(C_2H_5)_2$ | Cl | |
| 781 | $(CH_2)_3SCH_3$ | Cl | |
| 782 | $(CH_2)_3SC_2H_5$ | Cl | |
| 783 | $CH_2C_6H_5$ | Cl | |
| 784 | $CH_2CH_2C_6H_5$ | Cl | |
| 785 | $CH(CH_3)C_6H_5$ | Cl | |
| 786 | $CH(C_6H_5)_2$ | Cl | |
| 787 | $C_6H_5$ | Cl | |
| 788 | $C_6H_4$-(2)-Cl | Cl | |
| 789 | $C_6H_4$-(3)-Cl | Cl | |
| 790 | $C_6H_4$-(4)-Cl | Cl | |
| 791 | $C_6H_4$-(2)-$OCH_3$ | Cl | |
| 792 | $C_6H_4$-(3)-$OCH_3$ | Cl | |
| 793 | $C_6H_4$-(4)-$OCH_3$ | Cl | |
| 794 | $C_6H_4$-(2)-$OC_2H_5$ | Cl | |
| 795 | $C_6H_4$-(3)-$OC_2H_5$ | Cl | |
| 796 | $C_6H_4$-(4)-$OC_2H_5$ | Cl | |
| 797 | $C_6H_4$-(2)-$NO_2$ | Cl | |
| 798 | $C_6H_4$-(3)-$NO_2$ | Cl | |
| 799 | $C_6H_4$-(4)-$NO_2$ | Cl | |
| 800 | $CH_2-COOCH_3$ | Cl | |
| 801 | $CH_2-COOC_2H_5$ | Cl | |
| 802 | $N=CH-N(CH_3)_2$ | Cl | |
| 803 | $N(CH_3)_2$ | Cl | |
| 804 | $N(C_2H_5)_2$ | Cl | |
| 805 | $CH_3$ | Br | |
| 806 | $C_2H_5$ | Br | |
| 807 | n-$C_3H_7$ | Br | |
| 808 | iso-$C_3H_7$ | Br | |
| 809 | n-$C_4H_9$ | Br | |
| 810 | n-$C_{13}H_{17}$ | Br | |
| 811 | Cyclo-$C_6H_{11}$ | Br | |
| 812 | $C_6H_5$ | Br | |
| 813 | $C_2H_4Br$ | Br | |
| 814 | $N(CH_3)_2$ | Br | |
| 815 | $N(C_2H_5)_2$ | Br | |

EXAMPLE 816

4-chloro-3,5-dicyano-2-dimethylformamidino-1-methylpyrrole 4.8 g of 4-chloro-3-cyano-2-dimethylformamidino-5-formyl-1-methylpyrrole (Example 143) and 1.8 g of copper(I) cyanide in 50 ml of DMF were refluxed for 5 days. The reaction mixture was cooled and then filtered, and 200 ml of water were added to the filtrate. The precipitate was filtered off with suction, washed and dried. 1.4 g (30% of theory) of the compound of the formula

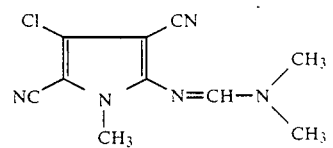

of melting point 180° to 184° C. were obtained The IR, NMR, UV and mass spectra and the elemental analysis are consistent with the structural formula.

The compounds listed in Table 8 are obtained in a similar manner to Example 816.

TABLE 8

| Example No. | L¹ | L² | Melting point [°C.] |
|---|---|---|---|
| 816 | $CH_3$ | Cl | |
| 817 | $C_2H_5$ | Cl | |
| 818 | n-$C_3H_7$ | Cl | |
| 819 | iso-$C_3H_7$ | Cl | |
| 820 | n-$C_4H_9$ | Cl | |
| 821 | iso-$C_4H_9$ | Cl | |
| 822 | sec-$C_4H_9$ | Cl | |
| 823 | n-$C_5H_{11}$ | Cl | |
| 824 | Neo-$C_5H_{11}$ | Cl | |
| 825 | n-$C_6H_{13}$ | Cl | |
| 826 | n-$C_7H_{15}$ | Cl | |
| 827 | n-$C_8H_{17}$ | Cl | |
| 828 | n-$C_9H_{19}$ | Cl | |
| 829 | n-$C_{10}H_{21}$ | Cl | |
| 830 | n-$C_{11}H_{23}$ | Cl | |
| 831 | n-$C_{12}H_{25}$ | Cl | |
| 832 | n-$C_{13}H_{27}$ | Cl | |
| 833 | n-$C_{14}H_{29}$ | Cl | |
| 834 | n-$C_{15}H_{31}$ | Cl | |
| 835 | n-$C_{16}H_{33}$ | Cl | |
| 836 | n-$C_{17}H_{35}$ | Cl | |
| 837 | n-$C_{18}H_{37}$ | Cl | |
| 838 | n-$C_{19}H_{39}$ | Cl | |
| 839 | n-$C_{20}H_{41}$ | Cl | |
| 840 | Cyclo-$C_3H_5$ | Cl | |
| 841 | Cyclo-$C_4H_7$ | Cl | |
| 842 | Cyclo-$C_5H_9$ | Cl | |
| 843 | Cyclo-$C_6H_{11}$ | Cl | |
| 844 | Cyclo-$C_7H_{13}$ | Cl | |
| 845 | Cyclo-$C_8H_{15}$ | Cl | |
| 846 | Cyclo-$C_9H_{17}$ | Cl | |
| 847 | Cyclo-$C_{10}H_{19}$ | Cl | |
| 848 | $CH_2-C_6H_5$ | Cl | |
| 849 | $CH_2CH_2C_6H_5$ | Cl | |
| 850 | $CH(CH_3)_2C_6H_5$ | Cl | |
| 851 | $CH(C_6H_5)_2$ | Cl | |
| 852 | $C_6H_5$ | Cl | |

EXAMPLE 853

5-Acetyl-2-acetylamino-4-acetyloxy-3-cyano-1-methyl-pyrrole 4.11 g of 2-amino-3-cyano-1-methylpyrrolin-4-one (Example 1) and 4.92 g of sodium acetate were refluxed in 50 ml of acetic anhydride for one hour. 150 ml of water were added and the mixture was then boiled for a further 30 minutes and then cooled to room temperature. The precipitate was filtered off with suction, washed and dried. 6.7 g (85% of theory) of the compound of the formula

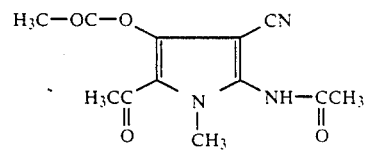

of melting point 140° to 141° C. were obtained. The IR, NMR, UV and mass spectra and the elemental analysis are consistent with the structural formula.

The compounds listed in Table 9 are obtained in a similar manner to Example 853

TABLE 9

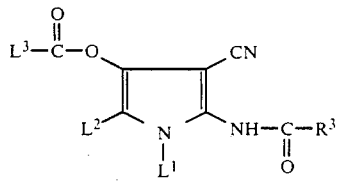

| Example No. | $L^1$ | $L^2$ | $L^3$ | Melting point [°C.] |
|---|---|---|---|---|
| 853 | $CH_3$ | $COCH_3$ | $CH_3$ | |
| 854 | $C_2H_5$ | $COCH_3$ | $CH_3$ | |
| 855 | $n-C_3H_7$ | $COCH_3$ | $CH_3$ | |
| 856 | $iso-C_3H_7$ | $COCH_3$ | $CH_3$ | |
| 857 | $n-C_4H_9$ | $COCH_3$ | $CH_3$ | |
| 858 | $iso-C_4H_9$ | $COCH_3$ | $CH_3$ | |
| 859 | $sec-C_4H_9$ | $COCH_3$ | $CH_3$ | |
| 860 | $n-C_5H_{11}$ | $COCH_3$ | $CH_3$ | |
| 861 | $Neo-C_5H_{11}$ | $COCH_3$ | $CH_3$ | |
| 862 | $n-C_6H_{13}$ | $COCH_3$ | $CH_3$ | |
| 863 | $n-C_7H_{15}$ | $COCH_3$ | $CH_3$ | |
| 864 | $n-C_8H_{17}$ | $COCH_3$ | $CH_3$ | |
| 865 | $n-C_9H_{19}$ | $COCH_3$ | $CH_3$ | |
| 866 | $n-C_{10}H_{21}$ | $COCH_3$ | $CH_3$ | |
| 867 | $n-C_{11}H_{23}$ | $COCH_3$ | $CH_3$ | |
| 868 | $n-C_{12}H_{25}$ | $COCH_3$ | $CH_3$ | |
| 869 | $n-C_{13}H_{27}$ | $COCH_3$ | $CH_3$ | |
| 870 | $n-C_{14}H_{29}$ | $COCH_3$ | $CH_3$ | |
| 871 | $n-C_{15}H_{31}$ | $COCH_3$ | $CH_3$ | |
| 872 | $n-C_{16}H_{33}$ | $COCH_3$ | $CH_3$ | |
| 873 | $n-C_{17}H_{35}$ | $COCH_3$ | $CH_3$ | |
| 874 | $n-C_{18}H_{37}$ | $COCH_3$ | $CH_3$ | |
| 875 | $n-C_{19}H_{39}$ | $COCH_3$ | $CH_3$ | |
| 876 | $n-C_{20}H_{41}$ | $COCH_3$ | $CH_3$ | |
| 877 | $CH_2CH=CH_2$ | $COCH_3$ | $CH_3$ | |
| 878 | $CH_2C\equiv CH$ | $COCH_3$ | $CH_3$ | |
| 879 | $Cyclo-C_3H_5$ | $COCH_3$ | $CH_3$ | |
| 880 | $Cyclo-C_4H_7$ | $COCH_3$ | $CH_3$ | |
| 881 | $Cyclo-C_6H_{11}$ | $COCH_3$ | $CH_3$ | |
| 882 | $Cyclo-C_7H_{13}$ | $COCH_3$ | $CH_3$ | |
| 883 | $Cyclo-C_8H_{15}$ | $COCH_3$ | $CH_3$ | |
| 884 | $Cyclo-C_9H_{17}$ | $COCH_3$ | $CH_3$ | |
| 885 | $Cyclo-C_{10}H_{19}$ | $COCH_3$ | $CH_3$ | |
| 886 | $CH_2CH_2OCOCH_3$ | $COCH_3$ | $CH_3$ | |
| 887 | $CH_2CH_2OCH_3$ | $COCH_3$ | $CH_3$ | |
| 888 | $CH_2CH_2OC_2H_5$ | $COCH_3$ | $CH_3$ | |
| 889 | $CH_2CH_2NHCOCH_3$ | $COCH_3$ | $CH_3$ | |
| 890 | $CH_2CH_2N(CH_3)_2$ | $COCH_3$ | $CH_3$ | |
| 891 | $CH_2CH_2N(C_2H_5)_2$ | $COCH_3$ | $CH_3$ | |
| 892 | $CH_2CH_2SCH_3$ | $COCH_3$ | $CH_3$ | |
| 893 | $CH_2CH_2SC_2H_5$ | $COCH_3$ | $CH_3$ | |
| 894 | $(CH_2)_3OCOCH_3$ | $COCH_3$ | $CH_3$ | |
| 895 | $(CH_2)_3OCH_3$ | $COCH_3$ | $CH_3$ | |
| 896 | $(CH_2)_3OC_2H_5$ | $COCH_3$ | $CH_3$ | |
| 897 | $(CH_2)_3NHCOCH_3$ | $COCH_3$ | $CH_3$ | |
| 898 | $(CH_2)_3N(CH_3)_2$ | $COCH_3$ | $CH_3$ | |
| 899 | $(CH_2)_3N(C_2H_5)_2$ | $COCH_3$ | $CH_3$ | |
| 900 | $(CH_2)_3SCH_3$ | $COCH_3$ | $CH_3$ | |
| 901 | $(CH_2)_3SC_2H_5$ | $COCH_3$ | $CH_3$ | |
| 902 | $CH_2C_6H_5$ | $COCH_3$ | $CH_3$ | |
| 903 | $CH_2CH_2C_6H_5$ | $COCH_3$ | $CH_3$ | |
| 904 | $CH(CH_3)C_6H_5$ | $COCH_3$ | $CH_3$ | |
| 905 | $CH(C_6H_5)_2$ | $COCH_3$ | $CH_3$ | |
| 906 | $C_6H_5$ | $COCH_3$ | $CH_3$ | |

TABLE 9-continued

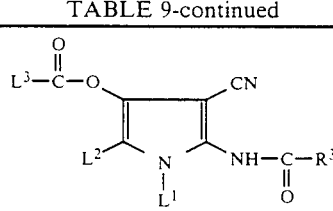

| Example No. | $L^1$ | $L^2$ | $L^3$ | Melting point [°C.] |
|---|---|---|---|---|
| 907 | $C_6H_4$-(2)-Cl | $COCH_3$ | $CH_3$ | |
| 908 | $C_6H_4$-(3)-Cl | $COCH_3$ | $CH_3$ | |
| 909 | $C_6H_4$-(4)-Cl | $COCH_3$ | $CH_3$ | |
| 910 | $C_6H_4$-(2)-$NO_2$ | $COCH_3$ | $CH_3$ | |
| 911 | $C_6H_4$-(3)-$NO_2$ | $COCH_3$ | $CH_3$ | |
| 912 | $C_6H_4$-(4)-$NO_2$ | $COCH_3$ | $CH_3$ | |
| 913 | $C_6H_4$-(2)-CN | $COCH_3$ | $CH_3$ | |
| 914 | $C_6H_4$-(3)-CN | $COCH_3$ | $CH_3$ | |
| 915 | $C_6H_4$-(4)-CN | $COCH_3$ | $CH_3$ | |
| 916 | $C_6H_4$-(2)-$COOCH_3$ | $COCH_3$ | $CH_3$ | |
| 917 | $C_6H_4$-(3)-$COOCH_3$ | $COCH_3$ | $CH_3$ | |
| 918 | $C_6H_4$-(4)-$COOCH_3$ | $COCH_3$ | $CH_3$ | |
| 919 | Pyrid-2-yl | $COCH_3$ | $CH_3$ | |
| 920 | Pyrid-3-yl | $COCH_3$ | $CH_3$ | |
| 921 | Pyrid-4-yl | $COCH_3$ | $CH_3$ | |
| 922 | $CH_2$—$COOCH_3$ | $COCH_3$ | $CH_3$ | |
| 923 | $CH_2$—$COOC_2H_5$ | $COCH_3$ | $CH_3$ | |
| 924 | $NHCOCH_3$ | $COCH_3$ | $CH_3$ | |
| 925 | $N(CH_3)_2$ | $COCH_3$ | $CH_3$ | |
| 926 | $N(C_2H_5)_2$ | $COCH_3$ | $CH_3$ | |
| 927 | $CH_3$ | $CH_3$ | $CH_3$ | |
| 928 | $C_2H_5$ | $CH_3$ | $CH_3$ | |
| 929 | iso-$C_3H_7$ | $CH_3$ | $CH_3$ | |
| 930 | $CH_2CH=CH_2$ | $CH_3$ | $CH_3$ | |
| 931 | Cyclo-$C_6H_{11}$ | $CH_3$ | $CH_3$ | |
| 932 | $CH_2CH_2OCOCH_3$ | $CH_3$ | $CH_3$ | |
| 933 | $CH_2CH_2OCH_3$ | $CH_3$ | $CH_3$ | |
| 934 | $C_6H_5$ | $CH_3$ | $CH_3$ | |
| 935 | Pyrid-3-yl | $CH_3$ | $CH_3$ | |
| 936 | $NHCOCH_3$ | $CH_3$ | $CH_3$ | |
| 937 | $CH_3$ | $C_6H_5$ | $CH_3$ | |
| 938 | $C_2H_5$ | $C_6H_5$ | $CH_3$ | |
| 939 | iso-$C_3H_7$ | $C_6H_5$ | $CH_3$ | |
| 940 | $CH_2CH=CH_2$ | $C_6H_5$ | $CH_3$ | |
| 941 | $CH_2CH_2OCOCH_3$ | $C_6H_5$ | $CH_3$ | |
| 942 | $CH_2CH_2OCH_3$ | $C_6H_5$ | $CH_3$ | |
| 943 | $C_6H_5$ | $C_6H_5$ | $CH_3$ | |
| 944 | $C_6H_4$-(4)-CN | $C_6H_5$ | $CH_3$ | |
| 945 | $NHCOCH_3$ | $C_6H_5$ | $CH_3$ | |
| 946 | $(CH_2)_3$—O—$CH_2C_6H_5$ | $COCH_3$ | $CH_3$ | |
| 947 | $(CH_2)_3$—O—$(CH_2)_2$—O—$C_6H_5$ | $COCH_3$ | $CH_3$ | |
| 948 | $CH_3$ | $COCH(CH_3)_2$ | $CH(CH_3)_2$ | |
| 949 | $CH_3$ | $COC_6H_5$ | $C_6H_5$ | |
| 950 | $CH_3$ | CO-n-$C_6H_{13}$ | n-$C_6H_{13}$ | |

EXAMPLE 951

4.1 g of 2-amino-3-cyano-1-methylpyrrolin-4-one (Example 1), 4.2 g of hydroxylammonium chloride and 5.1 g of sodium bicarbonate are refluxed in 100 ml of $H_2O$/ethanol (1:1) for 3 hours. The mixture was cooled to room temperature and then diluted with $H_2O$, and the precipitate was filtered off with suction. 4.2 g (83% of theory) of the compound of the formula

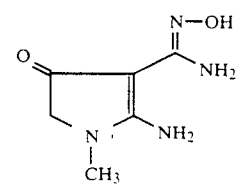

of melting point >260° C. were obtained. The IR, NMR, UV and mass spectra and the elemental analysis are consistent with the structural formula.

The compounds listed in the following Table 10 are obtained in a similar manner

TABLE 10

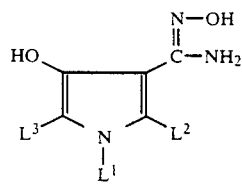

| Example No. | L¹ | L² | L³ | Melting point [°C.] |
|---|---|---|---|---|
| 952 | $C_2H_5$ | $NH_2$ | H | |
| 953 | n-$C_3H_7$ | $NH_2$ | H | |
| 954 | iso-$C_3H_7$ | $NH_2$ | H | |
| 955 | n-$C_4H_9$ | $NH_2$ | H | |
| 956 | iso-$C_4H_9$ | $NH_2$ | H | |
| 957 | sec-$C_4H_9$ | $NH_2$ | H | |
| 958 | n-$C_5H_{11}$ | $NH_2$ | H | |
| 959 | Neo-$C_5H_{11}$ | $NH_2$ | H | |
| 960 | n-$C_6H_{13}$ | $NH_2$ | H | |
| 961 | n-$C_7H_{15}$ | $NH_2$ | H | |
| 962 | n-$C_8H_{17}$ | $NH_2$ | H | |
| 963 | n-$C_9H_{19}$ | $NH_2$ | H | |
| 964 | n-$C_{10}H_{21}$ | $NH_2$ | H | |
| 965 | n-$C_{11}H_{23}$ | $NH_2$ | H | |
| 966 | n-$C_{12}H_{25}$ | $NH_2$ | H | |
| 967 | n-$C_{13}H_{27}$ | $NH_2$ | H | |
| 968 | n-$C_{14}H_{29}$ | $NH_2$ | H | |
| 969 | n-$C_{15}H_{31}$ | $NH_2$ | H | |
| 970 | n-$C_{16}H_{33}$ | $NH_2$ | H | |
| 971 | n-$C_{17}H_{35}$ | $NH_2$ | H | |
| 972 | n-$C_{18}H_{37}$ | $NH_2$ | H | |
| 973 | n-$C_{19}H_{39}$ | $NH_2$ | H | |
| 974 | n-$C_{20}H_{41}$ | $NH_2$ | H | |
| 975 | $CH_2CH=CH_2$ | $NH_2$ | H | |
| 976 | $CH_2C\equiv CH$ | $NH_2$ | H | |
| 977 | Cyclo-$C_3H_5$ | $NH_2$ | H | |
| 978 | Cyclo-$C_4H_7$ | $NH_2$ | H | |
| 979 | Cyclo-$C_5H_9$ | $NH_2$ | H | |
| 980 | Cyclo-$C_6H_{11}$ | $NH_2$ | H | |
| 981 | Cyclo-$C_7H_{13}$ | $NH_2$ | H | |
| 982 | Cyclo-$C_8H_{15}$ | $NH_2$ | H | |
| 983 | Cyclo-$C_9H_{17}$ | $NH_2$ | H | |
| 984 | Cyclo-$C_{10}H_{19}$ | $NH_2$ | H | |
| 985 | $CH_2CH_2OH$ | $NH_2$ | H | |
| 986 | $CH_2CH_2OCH_3$ | $NH_2$ | H | |
| 987 | $CH_2CH_2OC_2H_5$ | $NH_2$ | H | |
| 988 | $CH_2CH_2NH_2$ | $NH_2$ | H | |
| 989 | $CH_2CH_2N(CH_3)_2$ | $NH_2$ | H | |
| 990 | $CH_2CH_2N(C_2H_5)_2$ | $NH_2$ | H | |
| 991 | $CH_2CH_2SCH_3$ | $NH_2$ | H | |
| 992 | $CH_2CH_2SC_2H_5$ | $NH_2$ | H | |
| 993 | $(CH_2)_3OH$ | $NH_2$ | H | |
| 994 | $(CH_2)_3OCH_3$ | $NH_2$ | H | |
| 995 | $(CH_2)_3OC_2H_5$ | $NH_2$ | H | |
| 996 | $(CH_2)_3NH_2$ | $NH_2$ | H | |
| 997 | $(CH_2)_3N(CH_3)_2$ | $NH_2$ | H | |
| 998 | $(CH_2)_3N(C_2H_5)_2$ | $NH_2$ | H | |
| 999 | $(CH_2)_3SCH_3$ | $NH_2$ | H | |
| 1000 | $(CH_2)_3SC_2H_5$ | $NH_2$ | H | |
| 1001 | $CH_2C_6H_5$ | $NH_2$ | H | 205 (dec) |
| 1002 | $CH_2CH_2C_6H_5$ | $NH_2$ | H | 190 (dec) |
| 1003 | $CH(CH_3)C_6H_5$ | $NH_2$ | H | |
| 1004 | $CH(C_6H_5)_2$ | $NH_2$ | H | |
| 1005 | $C_6H_5$ | $NH_2$ | H | 210 (dec) |
| 1006 | $C_6H_4$-(2)-OH | $NH_2$ | H | |
| 1007 | $C_6H_4$-(3)-OH | $NH_2$ | H | |
| 1008 | $C_6H_4$-(4)-OH | $NH_2$ | H | |
| 1009 | $C_6H_4$-(2)-$OCH_3$ | $NH_2$ | H | |
| 1010 | $C_6H_4$-(3)-$OCH_3$ | $NH_2$ | H | 240 (dec) |
| 1011 | $C_6H_4$-(4)-$OCH_3$ | $NH_2$ | H | 220 (dec) |
| 1012 | $C_6H_4$-(2)-$OC_2H_5$ | $NH_2$ | H | |
| 1013 | $C_6H_4$-(3)-$OC_2H_5$ | $NH_2$ | H | |
| 1014 | $C_6H_4$-(4)-$OC_2H_5$ | $NH_2$ | H | |
| 1015 | $C_6H_4$-(2)-Cl | $NH_2$ | H | |
| 1016 | $C_6H_4$-(3)-Cl | $NH_2$ | H | |
| 1017 | $C_6H_4$-(4)-Cl | $NH_2$ | H | |
| 1018 | $C_6H_4$-(2)-$NO_2$ | $NH_2$ | H | |
| 1019 | $C_6H_4$-(3)-$NO_2$ | $NH_2$ | H | |
| 1020 | $C_6H_4$-(4)-$NO_2$ | $NH_2$ | H | |
| 1021 | $C_6H_4$-(2)-$NH_2$ | $NH_2$ | H | |

TABLE 10-continued

| Example No. | L¹ | L² | L³ | Melting point [°C.] |
|---|---|---|---|---|
| 1022 | $C_6H_4$-(3)-$NH_2$ | $NH_2$ | H | |
| 1023 | $C_6H_4$-(4)-$NH_2$ | $NH_2$ | H | |
| 1024 | $C_6H_4$-(2)-$CH_3$ | $NH_2$ | H | 190 (dec) |
| 1025 | $C_6H_4$-(3)-$CH_3$ | $NH_2$ | H | |
| 1026 | $C_6H_4$-(4)-$CH_3$ | $NH_2$ | H | |
| 1027 | $C_6H_4$-(2)-$C_2H_5$ | $NH_2$ | H | |
| 1028 | $C_6H_4$-(3)-$C_2H_5$ | $NH_2$ | H | |
| 1029 | $C_6H_4$-(4)-$C_2H_5$ | $NH_2$ | H | |
| 1030 | $C_6H_4$-(2)-CN | $NH_2$ | H | |
| 1031 | $C_6H_4$-(3)-CN | $NH_2$ | H | |
| 1032 | $C_6H_4$-(4)-CN | $NH_2$ | H | |
| 1033 | $C_6H_4$-(2)-$COOCH_3$ | $NH_2$ | H | |
| 1034 | $C_6H_4$-(3)-$COOCH_3$ | $NH_2$ | H | |
| 1035 | $C_6H_4$-(4)-$COOCH_3$ | $NH_2$ | H | |
| 1036 | Pyrid-2-yl | $NH_2$ | H | |
| 1037 | Pyrid-3-yl | $NH_2$ | H | |
| 1038 | Pyrid-4-yl | $NH_2$ | H | |
| 1039 | $(CH_2)_2$—$C_6H_3$-(3)-Cl-(2)-$CH_3$ | $NH_2$ | H | |
| 1040 | $(CH_2)_2$—$C_6H_4$-(3,4)-$(OCH_3)_2$ | $NH_2$ | H | |
| 1041 | $(CH_2)_2$—$C_6H_3$-(2)-Cl | $NH_2$ | H | |
| 1042 | $C_6H_3$-(3,4)-$Cl_2$ | $NH_2$ | H | |
| 1043 | $CH_2$—$COOCH_3$ | $NH_2$ | H | |
| 1044 | $CH_2$—$COOC_2H_5$ | $NH_2$ | H | |
| 1045 | $NH_2$ | $NH_2$ | H | |
| 1046 | $N(CH_3)_2$ | $NH_2$ | H | |
| 1047 | $N(C_2H_5)_2$ | $NH_2$ | H | |
| 1048 | H | $N(CH_3)_2$ | H | |
| 1049 | H | $N(C_2H_5)_2$ | H | |
| 1050 | H | $N(n\text{-}C_3H_7)_2$ | H | |
| 1051 | H | $N(n\text{-}C_4H_9)_2$ | H | |
| 1052 | H |  | H | |
| 1053 | H | 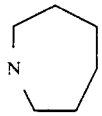 | H | |
| 1054 | H |  | H | |
| 1055 | H |  | H | |
| 1056 | H | 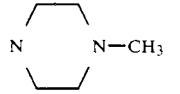 | H | |
| 1057 | H | (N-piperazinyl-N'-CH₃) | H | |
| 1058 | $CH_3$ | $NH_2$ | $CH_3$ | |
| 1059 | $C_2H_5$ | $NH_2$ | $CH_3$ | |
| 1060 | iso-$C_3H_7$ | $NH_2$ | $CH_3$ | |

TABLE 10-continued

Structure:

```
        N—OH
        ||
HO      C—NH₂
   \   /
    \ /
  L³—⟨pyrrole⟩—L²
     |
     N
     |
     L¹
```

| Example No. | L¹ | L² | L³ | Melting point [°C.] |
|---|---|---|---|---|
| 1061 | CH₂CH=CH₂ | NH₂ | CH₃ | |
| 1062 | Cyclo-C₆H₁₁ | NH₂ | CH₃ | |
| 1063 | CH₂CH₂OH | NH₂ | CH₃ | |
| 1064 | CH₂CH₂OCH₃ | NH₂ | CH₃ | |
| 1065 | CH₂C₆H₅ | NH₂ | CH₃ | |
| 1066 | C₆H₅ | NH₂ | CH₃ | |
| 1067 | C₆H₄-(4)-OCH₃ | NH₂ | CH₃ | |
| 1068 | C₆H₄-(2)-CH₃ | NH₂ | CH₃ | |
| 1069 | (3)-Pyridyl | NH₂ | CH₃ | |
| 1070 | NH₂ | NH₂ | CH₃ | |
| 1071 | H | N(CH₃)₂ | CH₃ | |
| 1072 | H | N(C₂H₅)₂ | CH₃ | |
| 1073 | H | piperidinyl | CH₃ | |
| 1074 | H | morpholinyl | CH₃ | |
| 1075 | CH₃ | NH₂ | C₆H₅ | |
| 1076 | C₂H₅ | NH₂ | C₆H₅ | |
| 1077 | iso-C₃H₇ | NH₂ | C₆H₅ | |
| 1078 | CH₂CH=CH₂ | NH₂ | C₆H₅ | |
| 1079 | CH₂CH₂OH | NH₂ | C₆H₅ | |
| 1080 | CH₂CH₂OCH₃ | NH₂ | C₆H₅ | |
| 1081 | CH₂C₆H₅ | NH₂ | C₆H₅ | |
| 1082 | C₆H₅ | NH₂ | C₆H₅ | |
| 1083 | C₆H₄-(4)-OCH₃ | NH₂ | C₆H₅ | |
| 1084 | C₆H₄-(4)-CN | NH₂ | C₆H₅ | |
| 1085 | NH₂ | NH₂ | C₆H₅ | |
| 1086 | H | N(CH₃)₂ | C₆H₅ | |
| 1087 | H | N(C₂H₅)₂ | C₆H₅ | |
| 1088 | H | piperidinyl | C₆H₅ | |
| 1089 | H | morpholinyl | C₆H₅ | |
| 1090 | (CH₂)₃—O—CH₂C₆H₅ | NH₂ | H | |
| 1091 | (CH₂)₃—O—(CH₂)₂—O—C₆H₅ | NH₂ | H | |

EXAMPLE 1092

10.0 g of 3-chloro-4-cyano-5-dimethylformamidino-2-formyl-1-methylpyrrole and 6.1 g of Meldrum's acid were stirred in 100 ml of dimethylformamide and 1 ml of piperidine at 50° C. for 15 hours. 200 ml of water were added and the precipitate was filtered off with suction and dried. 5.2 g (34% of theory) of the compound of the formula

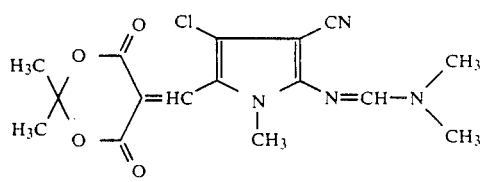

of melting point 199° C. were obtained. The IR, NMR, UV and mass spectra and the elemental analysis are consistent with the structural formula.

EXAMPLE 1093

6.6 g of malononitrile were dissolved in 200 ml of n-propanol. To this were added 5 g of sodium acetate and 11.9 g of 4-chloro-3-cyano-2-dimethylformamidino-5-formyl-1-methylpyrrole and the mixture was stirred at room temperature for 8 hours. The precipitate was filtered off with suction, washed with n-propanol and dried. 13.2 g (92% of theory) of the compound of the formula

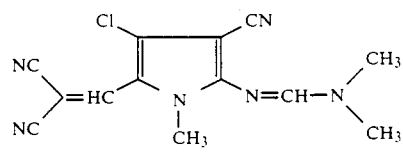

of melting point 180° C. were obtained. The IR, NMR, UV and mass spectra and the elemental analysis are consistent with the structural formula.

The compounds listed in the following Table 11 are obtained in a similar manner.

TABLE 11

| Example No. | $L^1$ | $L^2$ | $L^3$ | Melting point [°C.] |
|---|---|---|---|---|
| 1094 | $CH_3$ | $CH=C(COOCH_3)_2$ | $N=CH-N(CH_3)_2$ | 175 |
| 1095 | $C_2H_5$ | $CH=C(COOCH_3)_2$ | $N=CH-N(CH_3)_2$ | |
| 1096 | $C_6H_5$ | $CH=C(COOC_2H_5)_2$ | $N=CH-N(CH_3)_2$ | |
| 1097 | $CH(CH_3)_2$ | $CH=C(COOC_2H_5)_2$ | $NH_2$ | |
| 1098 | $C_2H_5$ | $CH=C(CN)_2$ | $N=CH-N(CH_3)_2$ | |
| 1099 | $n-C_4H_9$ | $CH=C(CN)_2$ | $N=CH-N(CH_3)_2$ | |
| 1100 | $CH_3$ | $CH=C(COOCH_3)(CN)$ | $N=CH-N(CH_3)_2$ | |
| 1101 | $C_6H_5$ | $CH=C(COOC_2H_5)(CN)$ | $NH_2$ | |
| 1102 | $C_6H_5CH_2$ | $CH=C(COOCH_3)(CN)$ | $N=CH-N(CH_3)_2$ | |
| 1103 | $C_6H_5$ | $CH=C(COOCH_3)(CN)$ | $NH_2$ | |
| 1104 | $CH_3$ | (barbiturate-type structure with N—CH₃) | $N=CH-N(CH_3)_2$ | |
| 1105 | $C_2H_5$ | (barbiturate-type structure with N—CH₃) | $NH_2$ | |
| 1106 | $CH_3$ | $CH=C(CONHCH_3)(CN)$ | $N=CH-N(CH_3)_2$ | |
| 1107 | $C_6H_5$ | $CH=C(COCH_3)(CN)$ | $NH_2$ | |
| 1108 | Cyclo-$C_6H_{11}$ | $CH=C(COC_6H_5)(CN)$ | $N=CH-N(CH_3)_2$ | |
| 1109 | $CH_3$ | $CH=C(C_6H_5)(CN)$ | $N=CH-N(CH_3)_2$ | |
| 1110 | $CH(CH_3)_2$ | (Meldrum's acid–type structure with $CH_3, CH_3$) | $N=CH-N(CH_3)_2$ | |
| 1111 | $CH_3$ | (Meldrum's acid–type structure with $CH_3, CH_3$) | $NH_2$ | |

TABLE 11-continued

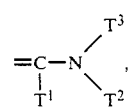

| Example No. | L¹ | L² | L³ | Melting point [°C.] |
|---|---|---|---|---|
| 1112 | CH(CH₃)₂ | 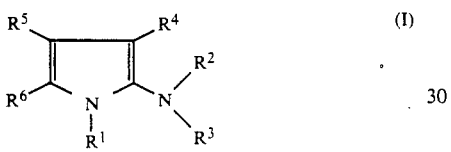 | NH₂ | |
| 1113 | CH₃ | CH=CH—NO₂ | N=CH—N(CH₃)₂ | |
| 1114 | CH(CH₃)₂ | CH=C(CH₃)—NO₂ | N=CH—N(CH₃)₂ | |

We claim:
1. A pyrrole derivative of the formula I

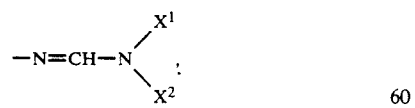

or the tautomer thereof, where $R^1$ is hydrogen, $C_1$-$C_{20}$-alkyl which can be substituted with $C_1$-$C_5$-alkylthio, phenoxy, halogen, hydroxyl, amino, $C_1$-$C_4$ mono- or dialkylamino, pyrrolidino, $C_1$-$C_5$-alkoxycarbonyl, or phenyl which can be substituted with $C_1$-$C_4$-alkyl, $C_1$-$C_4$-alkoxy, halogen, nitro, hydroxyl, or amino; $C_1$-$C_{20}$-alkyl which can be substituted with $C_1$-$C_5$-alkylthio, phenoxy, halogen, hydroxyl, amino, $C_1$-$C_4$ mono- or dialkylamino, pyrrolidino, $C_1$-$C_5$-alkoxycarbonyl, or phenyl which can be substituted with $C_1$-$C_4$-alkyl, $C_1$-$C_4$-alkoxy, halogen, nitro, hydroxyl, or amino and interrupted by one or more oxygen; $C_3$-$C_6$-alkenyl which can be substituted with fluorine, chlorine, or bromine; $C_3$-$C_6$-alkynyl which can be substituted with fluorine, chlorine, or bromine; $C_3$-$C_{10}$-cycloalkyl which can be substituted with fluorine, chlorine, or bromine; phenyl which can be substituted with $C_1$-$C_4$-alkyl, $C_1$4 $C_4$-alkoxy, halogen, nitro, hydroxyl, or amino; thienyl, amino, $C_1C_4$-alkanoylamino, benzoylamino, $C_1C_4$-dialkylamino or $$-N=CH-N\begin{matrix}X^1\\X^2\end{matrix},$$

where $X^1$ is $C_1$-$C_4$-alkyl or phenyl, and $X^2$ is $C_1$4 $C_4$-alkyl, is hydrogen, $C_1$-$C_4$-alkyl, benzyl, $C_3$-$C_6$-alkenyl, $C_5$-$C_7$-cycloalkyl, or phenyl which can be substituted with $C_1$-$C_4$-alkyl, $C_1$-$C_4$-alkoxy, halogen, nitro, hydroxyl, or amino;

$R^3$ is hydrogen, $C_1$-$C_4$-alkyl, benzyl or $C_3$-$C_6$-alkenyl, or $R^2$ and $R^3$ together are $$=C-N\begin{matrix}T^3\\T^2\end{matrix},$$

where $T^1$ is hydrogen, $C_1$-$C_4$-alkyl or phenyl, $T^2$ is $C_1$-$C_4$-alkyl, or phenyl which can be substituted with $C_1$-$C_4$-alkyl, $C_1$-$C_4$-alkoxy, halogen, nitro, hydroxyl, or amino; and $T^3$ is $C_1C_4$-alkyl, or $R^2$ and $R^3$ together with the nitrogen connecting them is pyrrolidino, $R^4$ is cyano, carbamoyl, $C_1$-$C_4$-mono- or dialkylcarbamoyl, thiocarbamoyl, $C_1$-$C_4$-mono- or dialkylthiocarbamoyl or

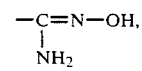

$R^5$ is halogen, hydroxyl, $C_1$-$C_{20}$-alkanoyloxy, or benzoyloxy and $R^6$ is hydrogen, $C_1$-$C_4$-alkyl, $C_1$-$C_4$-alkoxy, halogen, nitro, hydroxyl, or amino; cyano, halogen, nitro, hydroxysulfonyl, $C_1$-$C_{10}$-alkanoyl, benzoyl, or

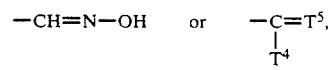

where $T^4$ is $C_1$-$C_4$-alkyl, or phenyl which can be substituted with $C_1$-$C_4$-alkyl, $C_1$-$C_4$-alkoxy, halogen, nitro, hydroxyl, or amino; and $T^5$ is the radical of an active methylene compound, hydroxylimino or N—$X^3$ where $X^3$ is $C_1$-$C_{20}$-alkyl which can be substituted with $C_1$-$C_5$-alkylthio, phenoxy, halogen, hydroxyl, amino, $C_1$-$C_4$ mono-or dialkylamino, pyrrolidino, $C_1$-$C_5$-alkoxycarbonyl, or phenyl which can be substituted with $C_1$-$C_4$-alkyl, $C_1$-$C_4$-alkoxy, halogen, nitro, hydroxyl, or amino; $C_1$-$C_{20}$-alkyl which can be substituted with $C_1$-$C_5$-alkylthio, phenoxy, halogen, hydroxyl, amino, $C_1$-$C_4$ mono- or dialkylamino, pyrrolidino, $C_1$-$C_5$-alkoxycarbonyl, or phenyl which can be substituted with $C_1$-$C_4$-alkyl, $C_1$-$C_4$-alkoxy, halogen, nitro, hydroxyl, or amino and interrupted by one or more oxygen; $C_3$-$C_6$-alkenyl which can be substituted with fluorine, chlorine, or bromine; $C_3$-$C_6$-alkynyl which can be substituted with fluorine, chlorine, or bromine; $C_3$-$C_{10}$-cycloalkyl which can be substituted with fluorine, chlorine, or bromine; phenyl which can be substituted with $C_1$-$C_4$-alkyl, $C_1$-$C_4$-alkoxy, halogen, nitro, hydroxyl, or amino; $C_1$-$C_4$-alkoxycarbonylmethyl, amino, $C_1C_4$-dialkylamino or phenylamino, with the proviso that $R^1$, $R^2$ and $R^3$ are not all hydrogen.

2. A pyrrole derivative as claimed in claim 1, wherein $R^1$ is hydrogen, $C_1$-$C_{15}$-alkyl, $C_5$-$C_7$-cycloalkyl, $C_3$-$C_5$-alkenyl, $C_2$-$C_5$-hydroxyalkyl, $C_2C_5$-halogenoalkyl, $C_1$-$C_5$-alkoxy-$C_2$-$C_5$-alkyl, phenoxy-$C_2$-$C_5$-alkoxy-$C_2$-$C_5$-alkyl, phenyl-$C_1$-$C_5$-alkoxy-$C_2$-$C_5$-alkoxy-$C_2$-$C_5$-alkyl, $C_1$-$C_5$-alkylthio-$C_2$-$C_5$-alkyl, $C_1$-$C_5$-dialkylamino-$C_2$-$C_5$-alkyl, phenyl-$C_1$-$C_5$-alkyl, $C_1$-$C_5$-alkoxycarbonyl-$C_1$-$C_5$-alkyl, $-(CH_2)_n-Y$ where n is from 1 to 5 and Y is pyrrolidino, phenyl, amino or $C_1$-$C_5$-dialkylamino, $R^2$ is hydrogen, $C_1$-$C_4$-alkyl, allyl, benzyl or phenyl, $R^3$ is hydrogen, $C_1$-$C_4$-alkyl, allyl or benzyl or $R^2 R^3$ together are

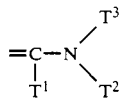

where $T^1$ is hydrogen, $C_1$-$C_4$-alkyl, $T^2$ is $C_1$-$C_4$-alkyl or phenyl, and $T^3$ is $C_1C_4$-alkyl, or $R^2$ and $R^3$ together with the nitrogen connecting them is pyrrolidino, $R^4$ is cyano, carbamoyl, thiocarbamoyl, or

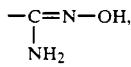

$R^5$ is fluorine, chlorine, bromine, hydroxyl, $C_1$-$C_6$-alkanoyloxy or benzoyloxy and $R^6$ is hydrogen, $C_1$-$C_4$-alkyl, phenyl, $C_1$-$C_6$-alkanoyl, benzoyl, cyano, chlorine, bromine, nitro, hydroxysulfonyl or

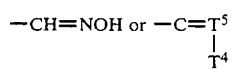

where $T^4$ and $T^5$ each have the meaning indicated in claim 1.

3. A pyrrole derivative as claimed in claim 1, wherein $R^1$ is hydrogen, $C_1$-$C_{10}$-alkyl, $C_3$-$C_4$-alkenyl, benzyl, phenyl or amino, $R^2$ is hydrogen, $C_1$-$C_4$-alkyl, allyl, benzyl or phenyl, $R^3$ is hydrogen, $C_1$-$C_4$-alkyl or allyl, or $R^2$ and $R^3$ together with the nitrogen connecting them is pyrrolidino, $R^4$ is cyano, carbamoyl, thiocarbamoyl or

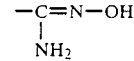

$R^5$ is chlorine, bromine, hydroxyl, $C_1$-$C_6$-alkanoyloxy or benzoyloxy and $R^6$ is hydrogen, $C_1$-$C_4$-alkyl, phenyl, $C_1$-$C_6$-alkanoyl, benzoyl, cyano or

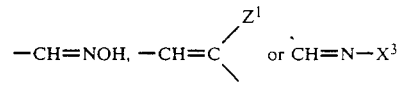

where $Z^1$ and $Z^2$ are identical or different and, independently of one another, are each cyano, $C_1$-$C_4$-alkoxycarbonyl or nitro, and $X^3$ has the meaning mentioned in claim 1.

4. A pyrrole compound as claimed in claim 1, wherein $R^1$ is $C_1$-$C_4$-alkyl, phenyl or amino and $R^2$ and $R^3$ are each hydrogen or $R^1$ is hydrogen, $R^2$ is methyl, ethyl, allyl, benzyl or phenyl, $R^3$ is methyl, ethyl or allyl or $R^2$ and $R^3$ together with the nitrogen connecting them is pyrrolidino, $R^4$ is cyano or carbamoyl, $R^5$ is chlorine, bromine or hydroxyl, $R^6$ is hydrogen, formyl, cyano or

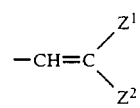

where $Z^1$ and $Z^2$ are identical or different and, independently of one another, are each cyano, $C_1$-$C_4$-alkyl, $C_1$-$C_4$-alkoxycarbonyl or nitro.

* * * * *